United States Patent [19]
Pollock et al.

[11] Patent Number: 6,030,817
[45] Date of Patent: *Feb. 29, 2000

[54] PRODUCTION OF NON-NATIVE BACTERIAL EXOPOLYSACCHARIDE IN A RECOMBINANT BACTERIAL HOST

[75] Inventors: Thomas J. Pollock, San Diego; Marcia Mikolajczak, Encinitas; Motohide Yamazaki, San Diego; Linda Thorne, Palomar; Richard W. Armentrout, La Jolla, all of Calif.

[73] Assignees: Shin-Etsu Bio, Inc., San Diego, Calif.; Shin-Etsu Chemical Co., Ltd., Tokyo, Japan

[ * ] Notice: This patent is subject to a terminal disclaimer.

[21] Appl. No.: 09/096,867

[22] Filed: Jun. 11, 1998

Related U.S. Application Data

[60] Provisional application No. 60/049,428, Jun. 12, 1997.
[51] Int. Cl.[7] ............................ C12P 19/06; C12P 19/04; C12N 1/20; C12N 5/00; C07H 21/04
[52] U.S. Cl. ........................ 435/104; 435/101; 435/252.3; 435/471; 435/320.1; 435/910; 536/23.2
[58] Field of Search ..................... 435/101, 104, 435/252.3, 320.1, 471, 910; 536/23.2

[56] References Cited

PUBLICATIONS

Pollock et al. (1994) Mechanism of Bacitracin Resistance in Gram–Negative Bacteria That Synthesize Exopolysaccharides. J. Bacteriol. 176 (20): 6229–6237.

Yamazaki et al. (1996) Linkage of Genes Essential for Synthesis of a Polysaccharide Capsule in Sphingomonas Strain S88. J. Bacteriol. 178 (9): 2676–2687.

Papoutsopolou (1994) Genetic Construction of *Xanthomonas campestris* and Xanthan Gum Production From Whey. Biotechnol. Letts. 16 (12): 1235–1240.

*Primary Examiner*—Lisa J. Hobbs
*Attorney, Agent, or Firm*—McAulay Nissen Goldberg Kiel & Hand, LLP

[57] ABSTRACT

A new recombinant bacteria for the production of exopolysaccharides is disclosed as well as a method for making the recombinant bacteria and making an exopolysaccharide from the bacteria by submerged aerobic fermentation of the bacteria utilizing a sugar substrate. The exopolysaccharides obtained from the inventive bacteria exhibit improved, more desirable or different properties from the exopolysaccharide produced by the non-recombinant bacteria from which the recombinant bacteria was derived. In addition, the present invention provides a method of producing bacterial exopolysaccharides by fermentation from sugar substrates that the bacteria which the exopolysaccharides are native to cannot utilize.

24 Claims, 2 Drawing Sheets

Xanthan gum

Sphingan S-88

SEQUENCE LISTING

<160> NUMBER OF SEQ ID NOS: 2

<210> SEQ ID NO 1
<211> LENGTH: 16075
<212> TYPE: DNA
<213> ORGANISM: Xanthomonas campestris
<300> PUBLICATION INFORMATION:

<400> SEQUENCE: 1

```
ggatccggtt gaggcggtaa caggggattg gcatggcatt gacgaaagcg gagatggccg      60
agcgtctgtt cgacgaagtc ggcctgaaca agcgtgaggc gaaggaattc gtcgacgcgt     120 tttctcgatgt gctgcgcgat gcactggagc agggccgtca ggtgaagttg tcgggcttcg     180
gcaacttcga tctgcggcgc aagaaccaac ggcccggtcg caatcccaag accggtgagg     240
aaattccgat ctcggccagg acggtggtga ccttccgccc cggccagaaa ctcaaggaac     300
gggtggaggc ttatgctgga tccgggcagt aatcgcgagc taccgccgat tccgccaag     360 cgctacttca ccatcggtga ggtgagcgag ctgtgcgacg tcaagccgca cgtgctgcgc     420
tattgggaaa ccgaatttcc gagcctggag gccagtcaag cggcgcgcaa ccgacgctac     480
```

-continued

```
taccagcggc acgatgtcgt gatggtgcgg cagattcgtg gcctgctgta cgagcagggt      540
tacaccatcg ggggcgcgcg tctgcgtctt gaagggatg gggccaagag cgagtcagcg       600
ctgagcaatc agatcatcaa gcaggtgcgc atggagcttg aagaagtcct gcagctgctg      660
cgacgctagg aaagcgccgc ataaagccgc tataatcgca ggccgcctca gggcgggacg      720
caacatcttc ggggtatagc gcagcctggt agcgcactag tctgggggac tagtggtcgt      780
cggttcgaat ccggctaccc cgaccaaaca acaggcctac gtcgcaagac gtgggccttt      840
ttgttgcgtc gcaacatgtc agttcgatgg cattccaggc tatgccacta tgcgcaacgg      900
catattgcaa ggcggcatat gcaagtcctg tacgcaatta tttcgcggtt caggctgcta      960
caagtcggga tcagcaggcg tccgtaagtg cccggaaacg ctagagttcg tatgctgaga     1020
atgacgaccc aggtcacgtt ctcttaacgt cgaggcgacg aacttgaatc aataggccaa     1080
cgccgtcaaa aaatggcgt gttgtgcctt gcgatgtgtt cgttctatgc catagtgcac      1140
tgcaacacgc gattcaacgt tggtcccggc acgcgtcggg atgcaacttc ctgtcgtacg     1200
ttcgtgctgg cgcctgagcc ggttgaatgc tgcgcgaggt cctgtcccac caacagagg     1260 cagccagcta cacgcatgaa gaaactgatc ggacgactcg tcgcaaggcc tcagcctggc     1320
tctgctctgc tcgatgtcgc tgggcgcttg cagcaccggc ccggagatgg cgtcttcgct     1380
gccgcatccg gacccgctgg caatgtccac ggtgcagccc gaataccgtc ttgcgccggg     1440
cgatctgttg ctggtgaagg tgtttcagat cgacgatctg gagcggcagg tccgcatcga     1500
ccagaacggt cacatctcac tgccgttgat tggcgacgtc aaggccgccg gtctgggcgt     1560
tggcgaactg gaaaagctgg tcgccgatcg gtatcgcgca ggctacctgc agcagccgca     1620
gatttcggta ttcgtgcagg agtccaacgg gcgtcgcgtc acggtcactg gtgcggtaga     1680
cgagccgggc atctacccgg tgatcggcgc caacctcacc ttgcagcagg cgatcgcgca     1740
ggccaagggt gtcagcacgg tggcaagccg cggcaacgtg atcgtgttcc gcatggtcaa     1800
cgggcaaaaa atgattgcgc ggttcgacct gaccgagatc gagaagggg ccaatccgga     1860 tcctgagatt tatggcggcg acattgtcgt ggtgtatcgc tcggatgcgc gcgtgtggtt     1920
gcgcaccatg ctggaactga ccccccttggt gatggtgtgg cgcgcttacc gatgagtatg     1980
aattcagaca atcgttcctc ttcgtcgcag cggtcatggt catctggaac tggcagatgt     2040
cgacttgatg gactactggc gcgccctggt ctcgcagctc tggctgatca tcctgatcgc     2100
cgtcggcgcg ctgttgctgg cattcggcat cacgatgttg atgcccgaga agtaccgcgc     2160
caccagcacc ctgcagatcg aacgtgactc gctcaatgtg gtgaacgtcg acaacctgat     2220
gccggtggaa tcgccgcagg atcgcgattt ctaccagacc cagtaccagt tgctgcagag     2280
ccgttcgctg gcgcgtgcgg tgatcccggga agccaagctc gatcaggagc ggcgttcaa      2340 ggagcaggtg gaggaggcgc tggccaaagc cgccgaaaag aatcccgagg cggtaagtc      2400 gctcgattcg cggcaggcga tcgtcgagcg cagcctcacc gatacgttgc tcgccgggct     2460
ggtggtcgag ccgatcctca actcgcgcct ggtgtacgtc aattacgatt cgccagaccc     2520
ggtgctggcc gccaagatcg ccaatacgta cccgaaggtg ttcatcgtca gcacccagga     2580
acgccgcatg aaggcgtctt cgtttgcgac acagtttctg gctgagcgcc tgaagcagtt     2640
gcgcgagaag gtcgaagact ctgaaaagga tctggtctcg tattcgaccg aagagcagat     2700
cgtgtcggtt ggcgatgaca agccctcgct gcctgcgcag aatctgaccg atctcaatgc     2760
gttgctggca tccgcacagg acgcccggat caaggccgag tcagcttggc ggcaggcttc     2820
```

-continued

```
cagtggcgat ggcatgtcat tgccgcaggt gttgagcagc ccgctgattc aaagcctgcg    2880
cagcgagcag gtgcgtctga ccagcgagta ccagcagaaa ctgtcgacct tcaagccgga    2940
ttacccggag atgcagcgcc tcaaggcgca gatcgaagag tcgcgtcgtc agatcaatgg    3000
cgaagtcatc aatatccgtc agtcgctgaa ggcgacctac gacgcctccg tgcatcagga    3060
gcagctgctc aacgaccgca tcgccggtct gcggtccaac gagctggatc tgcagagccg    3120
cagcatccgc tacaacatgc tcaagcgcga cgtcgacacc aaccgccagc tctacgatgc    3180
gctcctgcag cgctacaagg aaatcggcgt ggcgagcaac gtgggcgcca acaacgtgac    3240
catcgtcgat accgcagacg tgcctacgtc taagacttcg ccgaaactca aattgaacct    3300
cgcgttgggc ctgatctttg cgtattcct gggcgtggct gtggctctgg ttcgctactt    3360
cctgcgtggg ccttctccga ggtcgcggtt gaactgacat cgtgatgttg caaaacgatg    3420
gttaattgaa gtgacaactg attcagcgtg gaaaaggtgg gatcccgtaa ggtgcgggct    3480
ccctcgtttg aaggtttgtc tctgttgaaa caaagggctg tcgtgcgatc tggggtcggt    3540
aggtattacc gcggtgatcg gacgacagga tgattgaaag ctcgcgtgcg attcgtatgt    3600
tcccccgcat gcgccgtatc gagtttggag gacatcccca tgcttttggc agacttgagt    3660
agcgcgactt acacgacatc ctcgccgcga ttgttgtcca aatattcggc agccgccgac    3720
ctggtcctgc gcgtgttcga cctgaccatg gtcgttgcgt ccggactgat cgcataccgc    3780
atcgttttcg gtacctgggt acccgcagcg ccttatcggg tcgcgattgc gacaacgttg    3840
ttgtactcgg tgatctgctt tgcgttgttc ccgctgtatc gcagctggcg cggccgtgga    3900
ttgctgagtg agctggtggt gctgggtggc gcattcggcg gtgtgttttgc gctgttcgcg    3960 gtgcatgccc tgatcgtgca ggtgggtgag caggtgtcgc gtggttgggt cggcctgtgg    4020
ttcgtcggcg gcctggtgtc gctggtggcc gcacgcacct tgctgcgtgg cttcctcaat    4080
cacctgcgca cgcagggcgt ggatgtccag cgtgtggtgg tagtgggcct gcgtcatccg    4140
gtgatgaaga tcagtcatta cctgagccgt aatccctggg tcggcatgaa catggttggc    4200
tatttccgca cgccgtacga tctggcggtg gccgaacagc gccagggtct gccgtgcctg    4260
ggtgatcccg atgagctgat cgagtacctg aagaacaacc aggtggagca ggtgtggatc    4320
tcgctgccgc ttggcgagcg cgaccacatc aagcagctgc tgcagcgcct ggatcgctac    4380
ccgatcaacg tgaagctggt gcccgacctg ttcgacttcg gcctgttgaa ccagtctgcc    4440
gagcagatcg gcagcgtgcc ggtgatcaac ctgcgtcagg gtggcgtgga tcgtgacaac    4500
tacttcgtgg tcgccaaggc gctgcaggac aagatcctgg cggtgattgc gctgatgggc    4560
ctgtggccgc tgatgctggc cattgcgta ggcgtgaaga tgagctcgcc cggcccggtg    4620
ttcttccgtc agcgccgcca cggcctgggt ggccgcgagt tctacatgtt caagttccgc    4680
tcgatgcggg tgcatgacga tcatggcacc acgattcagc aggcgaccaa gaacgacacg    4740
cggattacgc gcttcggcag tttcctgcgc cgcagcagcc tggacgagct gccgcagatc    4800
ttcaatgtct tgggtggcag catgtcgatc gtgggcccgc gcccgcacgc cgcgcagcac    4860
aacacgcact atgaaaagct gatcaaccat tacatgcagc gtcactacgt caagccgggg    4920
attaccggtt gggcgcaggt caacggtttc gcgcggtgaga ccccgagct gcggacgatg    4980 aagaagcgca tccagtacga ccttgactac atccgtcgtt ggtcgctgtg gctggatatc    5040
cgcatcatcg tgctgacggc cgtgcgcgtg ctcggacaga agaccgcgta ctgatgacgg    5100
tggggagtgt gcgacctggc gcaccttgcg ccgcgggcgg ctgcatcgca gccgcctttc    5160
tctcgcgggc gctgacatgc tgattcaaat gagcgagcag gcgcgggtgc gttggcacaa    5220
```

-continued

```
cgcgctgatc gagctgaccc tgctgaccgg cgtgggctac aacctgctgc tggcgttgat    5280
caacgccaac gtgttcaccg tacgtccggt gatcacatat gcagtggaat ttctggtcta    5340
cgcagcctgt ttcctgctcg ggctgggctc gatgagccga cagcgcatcg cgatgatctt    5400
cggcgggcta ggcttgatcg tgacgctgat gttcgtgcgt ttcctggtca actggcagat    5460
cgaccccaag ttcttccgcg atgccctggt ggtctttgca tttgtcgtgc tggggtctgc    5520
ttacaccggc tcgttgccca agctgttcat acgcatgacg atcatcgtgt cattggtcgc    5580
tgcgttcgag ctggcgatgc cctcggctta tggcgatctg gtcaacccga agagcttctt    5640
cgtcaatgcg cgcggcatga gtgcagaagg gttctggaac gaggacagca atctgttcgt    5700
cagtgccaca cgacccggtg agcgcaactt cctcccaggc tcgaacctgc cacgcgcctc    5760
ttcctggttc atcgagccgg tgacgatggg caattacatc tgcttcttca ccgcgatcgt    5820
attgacgttc tggcgctgga tcggccgtc gatgctgatt ctgtctattg gattgatcgg    5880
cttcatgatt gtggcatccg acggccgact ggctgccggc acctgtgtgc tgatggtgct    5940
gctgtcgccg ttattgaaac ggatggatca gcggttggcg ttcctgttgt tcctgtttgt    6000
gatcgcctct gcctggctgc tggtgtggat gaccgggatt acggcctacc aggacaccac    6060 gatgggcgc atcttcttca ctgtgaattc gatgaacaat ctatcgttcg agtcgtggat    6120
gggcctggat tttgcgcagg cctaccggta tttcgacagc ggtatttctt actttattgc    6180
ttcgcagtcg attgtcggcg tgctggcgtt cctgctgtct tattcgttcc tgctgctgat    6240
gccgagcaag gaagggcagt tgttcaaaaa ccaggcgatg tttgcctttg cactgagcct    6300
gttggtgtct aacggctatt tctcgatcaa gacatcggcg ctgtggtggt ttgtctgcgg    6360
ctgcatgtgg cacctgatgc cagcagcgtc agccgtgccg gtgcgcgacg aaagcaagga    6420
agatccaacg gacaacggcg tgcatgtgcc gttgcccgca ggagcgccgc ggtgaatacg    6480
gtgacagggg catcggggac gtcggcgcct gtgcaggctg ccggcgcgcg tgccttcgcg    6540
agcggccgta gccgcgatcc acgtatcgat gcgaccaagg cgatcgcgat attgctggtg    6600
gtgttctgcc acgcaaaagg cgtgccgcac ggaatgaccc tgtttgccta cagctttcac    6660
gttccgcttt tcttcctcgt gtcgggttgg ctggctgccg gttatgcctc gcgcacaacc    6720
agcctgctgc agacaatcac caagcaggca cgtggtctgt tgctgcccta tgtcgtgttc    6780
tatctgcttg gatatgtgta ttggctgttg acgcgcaaca tcggcgagaa agctgcacgt    6840
tgggggagcc acccgtggtg ggagccgatc gtgtcgatgt ttaccggcgt cggcccggat    6900
ctgtatgtgc agccgccgct gtggttcctg ccggtgatgc tggtcaccgt gattggctac    6960
gttctgttgc ggcgctggat gccgccactg gtcattgcgg ctgtcgcagt tgttctcgcc    7020
tggttctgga tgaactggtt tccgctccag cacatgcgat tgttctgggg cctggatgtg    7080
ctaccggtgt cgctgtgctt ctacgcactg ggcgcgctgc tgatccacgt gtcgccgtat    7140
cttccaacct ccttgcctgg tagcgcgttg gtcaccgtag tgctggcagc attggttgcc    7200
tggctggccg gggtcaacgg ccgcatcgat gtcaacatgc tggaattcgg aaggcagcat    7260
gccgtattcc tgttgagtgc agtggcgggt tcgttgatgg tgatctgcgc ggcgcgcatg    7320
gtgcaggaat ggacatggct gcagtggatc gggcgcaaca ccttgctgat cctgtgcacg    7380
cacatgctgg tcttctttgt actgtctggt gttgcggcct tggcgggtgg gtttggtggg    7440
gcgcgcccag gccttggttg ggccatcttc gtgacgctct ttgcgctggt cgccagcgtt    7500
ccgctgcgct ggtttctgat gcgttttgcc ccctggacct tgggtgcacg tccggtgtcg    7560
```

-continued

```
gcatgacgac ggctgcgatc actgccggtc gcgtcgacac aatcgcctca actgtcgcgg    7620
agcgcgactg gcagatcgac gtggccaagg ctcttgcgat cattctggtc gcgctggggc    7680
acgccagtgg catgccgcct gcctacaagc tgtttgccta cagcttccat gtgcctctgt    7740
ttttcgttct ttccggctgg gtcggtgaac gcttcgggcg tcgtgcattt ggccggaaga    7800
cggtgggaaa gcttgcgcgc acgctgctga ttccctacgt cagcttttt ctggtggctt    7860 acggctactg gatactgagc gcagtgctca acggcacatc ccagtcctgg gctggccacc    7920
cctggtggca tccgtttgtt ggattgctgt gggccaatgg atccagcttg tatgtgctcc    7980
cggccttgtg gtttctcccc gcactgtttg tcgccaccgt tgtctacctg gcactgcgcg    8040
aagacctgag cgccgcagtg ctcgcggtct gcagtttgct ggttgtgtgg gcgtggacgc    8100
gttggttccc agggctgcgg ctgcgccttc cgtttgcact ggatgtgctg ccggtcgcgc    8160
tgttcttcat tgcagtcggc gcatggctgt cacgcttcgc agagagagtg cgcgcgcttc    8220
ctgcggtcgt ttgggtcgtc gcgttcccgg tcctggcatt cgcctggggg ggcgttgcag    8280
ccatgaacgg gcaggtggat gtcaataatc ttcagttcgg aaaatcgtcg ctcctgttcc    8340
tgatcgcaag cctgctgggt acagcaatga cgttgtgcat tgcctacttc atgcaagggt    8400
ggcgctggct gcgttggatc ggcgccaata cgctgctgat ccttggcacg cacacgttgg    8460
tgtttctggt cgtgaccagt gtcgtggtgc gaaccggggt gatcgatcgc aaactcatcg    8520
gtacacctgt ctgggcgctg gctctctgcg cctttgccat cgctgcctgc attcccatgc    8580
gtgccgtgct ggtgcgccgc gccctggatg ttgggattga aacgcaagtg agacattttc    8640
agaatcatca gtcgatgtgg cgtgttcgtg tgagtcaccg gcaaaggaga tcggcgcaat    8700
gaaagtcgtg catgtggtcc gccagttcca tccgtcgatc gggggggatgg aggaagtcgt    8760 gctgaacgtg gcacgtcagc atcaggccaa cagtgccgac acggttgaga tcgtgacgtt    8820
ggatcgtgtg ttcaccgatc cctctgcgca actggcgcag cacgagctcc atcagggggtt    8880 gtcgatcact cgcatcggct atcgtggttc atcgcggtac ccgatcgcgc cgtcggtgct    8940
gggggcgatc cgttcggcgg acgtggtgca tctgcatgcc attgatttttt tctacgacta    9000 cctggcgttg accaagccgc tgcacggcaa gccgatggtg gtctcgacgc atggcgggtt    9060
tttccacact gccatgcgt cgcgcatgaa gcagatctgg ttccagacgc tgacgcgtac    9120
ttctgcgctg gcctatgcgc gtgtgatcgc cactagcgag aatgacggcg atctgttcgc    9180
caaggtggtc gcgccgtcgc gcttgcgggt gatcgagaac ggtgtcgacg tggagaagta    9240
tgcagggcag ggcgctcgag cgccgggacg gaccatgctg tatttcgggc gttggtcggt    9300
caacaagggc ctgatcgaaa cgcttgaatt gctgcaggct gcgctcacgc gtgatccgca    9360
gtggcggttg atcatcgccg ggcgcgagta cgatttgaat gaggcggatc tgcgcaaggc    9420
catcgccgaa cgcggtttgc aggacaaggt gcagctgagc atgtcgccat cgcagcagca    9480
gttgtgcgcg ttgatgcagc aggcgcagtt cttcgtgtgc ctgtcgcggc atgagggggtt    9540 tgggattgcg gcggtggaag cgatgagcgc ggggttgatc ccgattctca gcgacattcc    9600
tccgttcgtg cggcttgcca ccgagtccgg acagggtgtg atcgtcaatc gcgacaggat    9660
tcaggccgcg gccgacagcg tgcaagcatt ggcgctgcag gccaatgcgg atttcgatgc    9720
gcgccgcacg gcgaccatgg cgtatgtggc gcgctacgac tggcggcacg tggtggggcg    9780
ttatatcgac gagtaccacg ctgcgctggg aacaccacgt acgcaggagg ccgtgcgatg    9840
agcgcgtctg cttcgctgcc agtgacgcgt gctgctgcgg cgccccggat cacggtgctg    9900
ttctccaccg aaaagccgaa cgccaacacc aacccgtatc tcacccagct ctacgatgcg    9960
```

```
ctgccggacg cggtgcagcc gcgcttcttt tcgatgcgcg aggcgttgtt gtcgcgctac    10020
gacgtgctgc atctgcactg gccggaatat ctgctgcgcc atcccagcaa gatgggcacg    10080
ctggccaagc aggcctgcgc tgccttgctg ctgatgaagt tgcagctgac cggcacgccg    10140
gtggtacgca ccttgcacaa cctggcgccg catgaagacc gcggctggcg ggagcgcgcg    10200
ctgctgcgct ggatcgatca gctcacgcgg cgctggatcc gcatcaacgc cactacaccg    10260
gtgcggccgc cgttcaccga caccatcctg cacggccatt accgcgactg gttcgcgacg    10320
atggagcaga gcaccacgtt gcctggtcgg ctgctgcatt ttggattgat ccggccgtac    10380
aagggcgttg aggtgttgct cgacgtcatg cgcggatgtg caggacccgc gcctgagcct    10440
gcgcatcgtc ggcaacccgg cgacgccagg atgcgcacgc tggtcgaaac cgcctgcgcg    10500
caggatgcac gtatcagtgc actgctggcc tatgtcgagg agccggtgct cgcgcgcgaa    10560
gtcagtgcct gcgaactggt ggtactgcca tacaagcaga tgcacaactc cggcaccttg    10620
ctgctggcgt tgtcgttggc gcggcccgtg cttgcgccgt ggagcgaatc gaacgccgcg    10680
atcgccgacg aagtcgggcc gggttgggtg ttcctgtacg aaggcgagtt cgatgcggcg    10740
ttgttgagcg gcatgctcga tcaggtgcgc gccgcgccgc gtggcccggc gcccgatctt    10800
tcacaacgtg attggccacg gatcgggcaa ttgcactatc gcacctactt ggaagcgctc    10860
ggcaaggatg gagacgccgc gctgtgaccg cagagacatc gaccatgact tccccaacac    10920
cgccgccgcg cagcctcggg tcgcgtgccg ctggcgccgc cgtgaccatg atcgggcagt    10980
cggccaagat gatcgtgcag ttcggcggca tcgtgctgct ggcacgcttg ttgacgccgt    11040
acgactacgg cttgatggcc atggtgaccg ccatcgtggg ggccgccgaa atcctgcgcg    11100
acttcggtct ctccgcagcc gccgtccagg cgaaacatgt cagccgcgag caacgcgaca    11160
acctgttctg gatcaatagc ggcatcggtc tgatgctgtc ggtggtggtg ttcgccagcg    11220
cgcactggat tgcggacttt tatcacgagc ccgcattggt gacgatttcg caggcattgg    11280
cggtgacctt cctgctcaac gggatgacca cccaataccg cgcacacctc agtcgggggc    11340
tgcgcttcgg tcaggtagcg ctgagcgatg tgggttcgca ggtgttgggg ttgggtgctg    11400
cagttgcggc cgccttggcc ggctggggct actgggcgtt gatcgtgcag caggtggtgc    11460
aggccatcgt gaacctgatt atcgctggcg catgtgcacg ctggttgccg cgcgggtacg    11520
cgcggcaggc gccgatgcgc gatttcatga gctttggctg gaacctgatg gcggcgcagc    11580
tgctcggcta tgcgagccgc aacgttggcc aggtgatcat cggctggagg accgggcccg    11640
acgcgctggg tctgtacaac cgtgccttcc agttgttgat gatgccgttg aatcagatca    11700
atgcgcctgc gactagtgtg gcgctgccgg tgttgtcgca attgcaggat gagcgcgagc    11760
gctacagcgc ttttctgttg cgcggccaga cggtcatggt gcatttgatc tttgcgctgt    11820
tcgcgtttgc ctgtgcactg gccatgccgc tcatcgtcct ggtgctgggt gagcagtggc    11880
gggaagcggt gccgctgttt caggtgttga cgctgggcgg tatcttccag acggcgtcgt    11940
acgcaaccta ctgggtgttc ctgtcgaagg ggttgatgcg cgagcagttg gtgtattcgt    12000
tggtcggtcg catcctgctc atcgcctgca tttttgttgg ctcccgctgg ggggccatgg    12060
gcgtggcgat cggctactca ttcggcctgc tgttgatctg gccgctgtcg ctggtctgga    12120
tcggcaagat cacggacgca ccggtcggtg cgttgttcgt caatgccatg cgtgcgctgg    12180
tggcctacgg tatcgccggc ggctgcgctt attacgcatc ggtcactgtc ggtggtccat    12240
tgtggcagca gctgctggtc ggcgccggcg cgatggcgct ggtctgtctg ctcgcattgg    12300
```

-continued

```
catggccggg attccggcgt gacgtggtcg ctatcgtcaa tatccgcaag ctgctcacgc    12360
aggcgaaggc gcgccgatga cactgcactg cggtactgga atgttggact cgaaacttc     12420 ccactcttgc aaaggacacg gcctatgagc gtctctcccg cagctccagc ttccggcatt    12480
cgccgtccct gctatctggt cttgtctgct cacgatttcc gcacgccacg tcgggctaac    12540
atccatttca tcaccgatca gttggctttg cgtggcacga cgcgtttttt ttcgttgcga    12600
tacagcagac tctcccgcat gaagggagat atgcgcctgc cgctggatga caccgcaaat    12660
accgttgtct cgcacaacgg tgtggactgt tacctgtggc gcacgacggt gcatccattc    12720
aatacacgcc ggagctggct acgtcctgtg aagacgcca tgttccgctg gtatgccgcg     12780
catccgccaa gcagttgct ggactggatg cgcgagtccg atgtcatcgt gtttgaaagc     12840
gggatcgcag tcgcattcat cgagcttgcc aagcgggtca atccggctgc caaactggtc    12900
tatcgcgcgt cggacgggct gagcaccatc aacgtggcgt cttacatcga gcgcgagttc    12960
gaccgcgtgg ctccgacgct ggacgtcatt gccttggtgt cgcccgcgat ggccgcagaa    13020
gtagcaagcc gcgacaacgt cttccatgta ggtcacggcg tggaccacaa cctcgatcag    13080
ctcggcgacc cgtcgccgta tgccgaaggc atccatgcag ttgcggtcgg gtcgatgctg    13140
tttgatcctg aattttcgt cgttgccagc aaggcctttc gcaagtgac cttccacgtg      13200 atcggctccg ggatgggccg ccatccgggc tacgcgaca atgtcattgt ctatggcgaa     13260
atgaagcacg cgcagacgat tggctatatc aagcacgcac gtttcggcat tgcgccttac    13320
gcgtccgagc aggtgccggt gtatctgca gacagctcaa tgaaattgct gcaatacgac     13380
tttttcggct tgccggcggt gtgcccgaat gctgtggtgg ggccgtacaa atcgcgcttc    13440
gggtacacgc caggcaatgc cgattcgtg attgccgcca ttacccaggc actggaagca     13500
ccgcgtgtac gttaccgcca gtgtctcaac tggtccgaca ccaccgaccg cgtgctcgac    13560
ccacgggcgt acccggaaac ccgtctttat ccgcaccccc ccaccgccgc gccgcagctc    13620
tcttcggagg cagcgctctc acattgagga ggcgttttt tgatcacgtt tgaaggagga    13680
tccctgtcat ggccaacgct ttactgcaga aatgggtgga acgggcggaa cgtcgcgcat    13740
tgttctggtg gcagcccaaa aacggtggcg tgaacatggg ggatcacctg tcgaaggtga    13800
tcgtgtcgtc cgtgttggcg ttgcaggaca agacacttct ggaaaaacgc gatttgcgcc    13860
agaagctgat cgcaaccggg tcggtgctgc atttcgccaa agatggcgac accgtgtggg    13920
gaagcggtat caacggcaag attccggccg agcgcaatac gttcagcacg ctggacgtac    13980
gcgcggtacg cggtcccaag acccgcgcat ttttgctgga acgtggcatc gcagtgcctg    14040
aggtctacga agacccggga ttgctgaccc cgatgttttt ccccgccgac gccctcggcc    14100
cggtcaccaa gcgcccgttc gcgatcgtgc cgcacttcaa cgagccggtt gagaagtaca    14160
gcgcctacgc cgagcatctg gtgtttccca acgtcaagcc ggccaccttc atgagtgcgc    14220
tgctgggtgc ggaatttgtc atcagcagtt cgctgcatgg cctgatcctg gccgaagcct    14280
atggcatccc ggcggtgtat ctggactggg gcaacggcga agaccgtttc aagtacgacg    14340
actactacca cggcaccggg cgcatgcaat ggcatgccgg ccacagcgtg gaagaatgca    14400
tggaactggg cggcaacggc agtttcgatc ttgaacgctt gcaggcagga ttgctggctg    14460 cgttcccta cgatttgtgg tgaaacgaca atgcatggcc agccagcagg tgtggagacg     14520
gcaacggtga gtgcagcgac acctgcgcaa ggggtggtga ttccgctggg cggcttcccg    14580
gtgttgtcga ccacgcagga agccttcgcg ctggatctgt tccatgcgct ggccgcgcat    14640
cagccgcgcc gggtgttttt cgcgaacacc aacttcatcg tgcagtgcca ggcgctgcgc    14700
```

```
gcgcgcatgc aggcgccggc agtgcgcatc gtcaacgatg ggatcggcat ggatctggcg    14760
gcgcgcctga tccatggccg ccggttcgcc ggcaacctca acggcaccga cctgattccg    14820
tacctttgcc gcgaggccgc gcagccgctc aagttcttcc tgctcggcgg ccgcccgggc    14880
gtgggcaaga ccgccgcggc gaccttgacc ggaacgctgg gccagcaggt cgtgggcatg    14940
tgcgatgggt atggcgaatt tgcggcggcg ggcgagggct tggccgagcg catcaatcgc    15000
tccggcgccg atgtgctgtt ggtggccttc ggcaacccgc tgcaggagcg gtggatcctg    15060
gaccacagcg aggccttgca ggtgccgctg gtgttcggcg tgggcgcctt gctggatttt    15120
ctctccggca ctgccaagcg cgcgcccaac tgggtgcgcc gtttgcatat ggaatggatg    15180
taccggctgc tcaacgagcc gcgccggttg ctcaagcgct acagctggga tctgctggtg    15240
ttcttccgca cctgcctgcg tgcgggcaaa cagctggcgt gatgcacggc ggcggtgtgt    15300
ggcctagcat gcgtgcatgc atccaaccgc cgccgcgctg attcgaacat tgggccttgc    15360
cccccatccg gagggcggcc actaccggcg cgtgtacgcg tcgacgcgcc aggtgctgga    15420
tgacagcggt gcgccgccgc gtccggcgct gaccgccatc cgcttcctgt tgtgcgcagg    15480
cgaagccagt cgctggcatc gggtggatgc cgaggagtgc tggcactggc agcaaggtgc    15540
gccgctggag ttgctgatct tcgacgaagc gagcgggcag ttgcggcgcg aagtgctgga    15600
cgccgcagag cgcggcgacg ccatgcacgt ggtgccggcc ggctgctggc aggcggcgcg    15660
ctcgctgggg gacttcaccc tggtgggctg cacggtttcg ccaggggttg tctgggaagg    15720
tttcgcgctg ctcgaagacg gctcgccgct ggcggcacag ctggccgcgt tggttgccga    15780
aggcgccgcg ccggagccgc caacgcttcc ctaacgcgtg cgggcccgcg ttcgcgtagt    15840
gtccgcgttc caaccgggag gcggtacgtg atgcagcgca gggggcggt gtggcgggca    15900 ggaatcgcgt tggtgtcgtt gttggcaccg atgctggcgt gtgccgtcga ggtggccgta    15960
caggcgccgg cagcgccgcc aacggtggtc gatctggaag ccatggtggt gcgcgggcag    16020
caacccggcc ccggcctgtg gaaggtcagc aagggcgacc acgtgctgtg gatcc        16075
```

<210> SEQ ID NO 2
<211> LENGTH: 28804
<212> TYPE: DNA
<213> ORGANISM: Sphingomonas sp. S88

<400> SEQUENCE: 2

```
ggatccactg gccgggaatt gccgagaatc ctccgatgaa gcgctcgtcg ggtaccagcg      60
tgccccgggg cgcatcgctt tgcgccggcg catcgccgcc gctgccgggc cggccattcc     120 agcgggtcc gggctgcaaa atcccgggc ctgcctttac gccatgcccg gcagccgagc      180
tgccgggcgc cgagcatgcg agcggcgtaa ccgatagggc gaggccccg cccagaaggg      240 tgcgacgtgt ggtatcgatc atgcggcgcg ctccaaaccg tgcgcgccgt gactacaacc     300
aaaaatgctg cgctgcgagc gggatcaggc gccccgtgcc tgcttcgagc ggtacagcag     360
cgcgaacgtc agccccacca gcatgaagaa gacttggtcg ttgtcggtct cgacagcac      420 gagcctggta ttgagcagca cgaccatcgt cgtcgcgacc gccagatgca gcggatagcc     480
ttgggagggg tccgtcaacc cggcgcggat caacagcccg gcacccagca ccatcgtacc     540
gtagaatgcg atgaagccga gcaccccgta atcgacggcc gtcgaaagga agccggagtc     600
gatcgacagg aacccgctct gggaacgcca tccgacacc tccgcggact ggaacggccc      660
gtagccgaat accggcgcgca tcgcgagctt gggcaagccc atgcggatct gctcgtggcg     720
```

```
cccgtcgttg ctcgcctggg tcgcgccgcc gccaagaacg cgattgtgta ccgcaggcac      780
taccatgatc atcaccgcga gaaccacggc gaaggccgga tacatcatcg tcgtggaaat      840
cccgacgagc ccgccacgct ccttgatcca gcgccgcagg ccccagagca acagataggt      900
ggcatgcgcc acgaccatgc cgaccatgct caggcgcgcg ccgctccaat aggcggacaa      960
taccatggcg agatcgaaca ggatcgtgag tgccagcgcc gacaccgacc ggctgttcac     1020
catcaggtgg atcgcgaagg gaatcgtcat cgccacgagt tcgcccaca ccagcgggtt     1080 cccgaacacg ttcatcacgc gatacgtgcc gcgcacctgc gaggtgagat gcaggatgac     1140
gctcggatcg ttgatctgca gccagctggg aatgtggccg acccacagaa cgtgctcggc     1200
ccggaactcg aagaagccga tcaccatcag cacggacacg cagcccagca tgttccgcac     1260
ccaccattcg ggtgtgcgcg tgttcgatcc caggcaccac agcgtcgcga agaagaacgg     1320
cgtgaccgtc agcgagatat tcaccaggcg cccgatcgaa acggatggct ggctggaaat     1380
gagcgacgcg atgatctgga tgatcaggaa gcccagcatg aagcgggcaa gccagggcga     1440
cgccgacagc gtcaccgcca tgtcgcgccg aaacttcggc gaaatcgaat agcacaccag     1500
cagaagaagc gtcgtcagca cgccgaacag gcggcggaag gagatccagg gcaggcccgc     1560
caccgacagc gacagatagt tcggccacac gatcgcgagg atcatgaaca ggacgtagca     1620
gcgcagcagc aacttggtgg gcgccttgtc ggcctccggg agcgcccaga tgacgaacag     1680
cgcgaggatc gccagcggcg cggcggcccc gaggagcatg ctgggcggca ggatcgccga     1740
aagcagcccg tagaccatcg acacgaacac gatcacggcg agcccgatga agcgccgccc     1800
gagcgtgacg agaccagagc gttgcgggtg atagagcggg agcaccgctc tggcggggaa     1860
gaacacgatg tcgcgcgccc ggcgcagggg ctgcaccacc cgcgccaagc cgccgctccc     1920
ccgaactcgc gccgatgtcg ccatgaccaa ccccttagat aatcggtatg ccgatcagcc     1980
gcaccgcgac catcgacacg aagcgcagga agaccgacgg caccgcgatc gcaatcgccg     2040
cgcctagtgc accataggc ggaatcagga ccagcgcgag tattgcggca aggataaccg     2100
acgacatggt cagcaccacg gccagacgct cgcgattggc catgacgagg acgccgccgc     2160
tcgacgcgaa gaccatcccg aacacctgcc caagcaccag cacctgcatc gcggcggcgc     2220
ccgcggtgaa ctgtttgccg aacaggccca tgatccaatg cggagcgacc agcaccgcca     2280
gggcgatggg cgaggcggcg accagcagcg cgagaatggt gatccggatg atgcgggcga     2340
tccgcttgac gtcgccctgt tcgtaggagg cggcaaagac cggatgcagg atcgtctcgg     2400
aggtggccga cagcaacttg agcgaggatg cgatctgata gcccacccgg aacagaccgg     2460
cttcggcggg gccgtgcgtc gcggcaagga tcacggtggc aaaccagtcg acgaagaagt     2520
tgttgacgtt ggtgatcagc accatgaagc cggggcgaag catcggccgg tccaacggct     2580
cggccggcgc ccaatcacgc gtcatgcggc ggacgatgat cgtcgcggca acatcgtca     2640 ccagccagcc gaccaggtac agcaccgacg gcagcagcgg attatgggca acgccgatca     2700
gcagcgcgcc ggccagcatc gccccaccca ggaaggtgcc gagcggccca tcgaccatct     2760
gcgacttgcc gatatccccc atgccgcgca gcgtcgtcga agcgagacgg caataggcgc     2820
tgaccggaat gagaaacccc atgatcagaa ggtccggcgc catggcgggg ctgcccagca     2880
ggttggtggc aatctgttgg tgaaacagca ggatcatcac catcaggacc aggccaccac     2940
ccaccgcgac ccgcgtggca tgccgcactg cggtacgcgc cacacccgtc cgattttgcg     3000
acacgcagac ggcacggtg cgcaccagga tggtatcgag gccgatcagc gacagaatga     3060
ccagcatctg cgcagtcgtg agcgccgtac cgaaggcacc gacgccggcg gggccaaagg     3120
```

```
cgcgggcgac cagccaggtg aaagcgaaac tggtgacggc gccgaagccc ttgacgccga    3180
agccgaccac catctgcccc cgcagccccc gcaggtgcaa cttgctacgt gtcacgttga    3240
atgcttgccc cacaggagat cccgtctgtg ccttatggca gggccctccc gggggcaagc    3300
ctgaggacgt catcgacgt gatagaagtc ctgcaccaac ttcttggtgg cgaacaggct    3360
attcgccacg gacaggctgc ccgtcgccga gacggcgca gtgccggccg cattcatggc    3420
gatcgcctgg gcgagcgaca cttgcgcgac ggacgccgtc gatgccgatc cccccagcgt    3480
cagcgtgccg gtggtcgccg ccggcagcgc cgtcgacgtg accggggtgc cgagaatggt    3540
tacggcgctg gcggccaagc tgctggtgag gctgggcttc acggtggtgg tcggctggct    3600
ggcggcggtc gccgcggcat tcagcgcaag gatctgggac gcactgaggg cagcgtcgcg    3660
catctcgatc tcgcccacgc tgccgctgaa gacagcgttg aacgggctgc cgatgtacag    3720
tccggcatat tcgaccgccc gcgtgctgcc gacgatcgtt cccgatccct tcaccacgcc    3780
atcgacatag atgatcgcct tgcccttcgc gctgtcatag gtcagcgcga tcttgtgggt    3840
ggccgtgtcg gtcatcttgg cgccgctcgt cgcgacggta tagctctgcc cggcggcatt    3900
cttgacggtg aagaccagtt cgccgtccgc ccggagcgag attccccagc tctggttgac    3960
gcccatgatc tggccgaccg cgcccgtcgc ggtggcacgc ttcatgtcga agttgagcgt    4020
gaaggcgggc agcgcgaaga gttgacgtga attgtcccgc gtaagctcga agccggtgcc    4080
ggtcttcacc tggaacatgc cgttgctgat ggcggtgaga tccagcgcct tcgtggtctc    4140
gtccgtgctc cagcgcgtct ggtccacgat tccggtcgca gtgaactgca gatccagcag    4200
caggttggcg ccggtcgagg tctgtgctgc cgcctgctcc ttggcgacct gcgcggcaaa    4260
cgcgctgcct gcaggcggct gatacccgac accactgacg atcaggttcg ccagttgcgc    4320
cttcgatccg gccatgagat cgccgatctt gcgaagagtg accgcgtccg ttgcaagcac    4380
ggcgttgttc gattgagtaa tgccgctcga cgttgcggtg atgacaacct ggtccacgac    4440
attgttggtg accttgccgc cggtcacgcc gtccaggcgg atccaatcgg cgatcgcatc    4500
catcttcgag atgatggtat tggagtccac ggtgacgttc ttgcccagaa cgacattgat    4560
gccgtgcgtg aaaccattct ggtacacgag attgtttttg atcgtgatgt tttcgtaggg    4620
aatgctggat tcattgccca tgaatacgcc ctggaaggcc aggccgtccc cctgcatcat    4680
cacgttattg gtgatcgtga tgttcgtgtt gcccttggtc ttgccgttcg tcatgaactg    4740
gatggcgtcg ggatgctcac cattcaccgg atagaggttg gtgaacatgt tgttgtcgat    4800
gacgacgttc gacgcttcgg cgaaattggt gtgatcgcgg cgattgtcgt ggaagttgtt    4860
gccctgcagg gtgacaccgt cgacggtgag gacgttcatc cccagggcga aatgatcgac    4920
cgaggaattc ttgatcgtca ccccttgct ttctcgcagc agaagccccc agcccatcga    4980
cttcgtcaca tcgcccgtac ccccgctcag ggtcacgccg tcgatcacga cattgctgga    5040
gccgatgatc cggttcgcgt aattatagtc ctgtgccggc tggaagtttt gtgcggccgt    5100
gacgttcttc accaccaggt tgctgctgtt gatgatctgc agggtcgtca cattcaccgg    5160
cttgctcgca tcgagcgagg tgatcgtgac gggcgtggtg aaggtcgtgg tgtgcacggt    5220 gatgacgta taggtccccg ccgcaagctt gatcgtctcg ccccctttcg cagccttgat    5280
ggcggcgtcc agttcgctct gattcctcac gatgatgtcc ggcatgtact ctaccctcgt    5340
tacgcgtcga ccccaatcga cctgcgatcc ctcggaccgt cttgtacctg ccaagccctg    5400
aaacggtggc taagaggcag ggttaatgcc ctgttttca agccgataac tggcagccct    5460
```

-continued

```
caaggcactg ccagcgtgcg ggcaacactc tcgacgccgc agtgcagcac gggtaagaac    5520
gaggcatgga agcctcgccc acacccgacg tcagcatcct ggtggttgcc taccactcgg    5580
ctccgttcat cggacaatgc atccgggcca tcgccgcggc ggcacaaggc acagcccacg    5640
aaatcctgct gatcgacaat ggcggcggcg acaccgaggc ggtggttcgt gccgagttcc    5700
cgcacgtgcg gatcgtgccg agcgagggca atatcggctt cggggcgggg aataaccggt    5760
gtgcggccca tgcccgcgcg ccgcggctgc tgctcgtcaa ccccgacgcc attccccgcc    5820
ccggcgcgat cgacctgctg gtcgccttcg ccaaggcgca cccggacgcg gcagcctggg    5880
gcgggcgttc ctattttccg aacggccagc tggaccatgc caacttcctc ccgctgccca    5940
cggtgcgcga tttcgtcgtg tcgatcttca gcagcagccc gatgcggcgc ggcggccttc    6000
ctgccgacgc caccgcgccc gggccggtcg aggtgctcaa cggcggcttc atgatggtcg    6060
atgcccgcgt gtggcgggag atcgacggct tcgacgaagg cttcttcctc tattcggagg    6120
aaatcgatct gttccagcgg atccgcgcgc ggggctattc cgtgctggtc gatccggctg    6180
tgggcgtggt gcacgacacc ggtggcgggc attcgctctc gcccactcgc gtgctgtttc    6240
tcaccaccgg ccgcatgcat tatgcccgca agcatttcgg ccacgtcggt gccgtcgtga    6300
cgggctgggc actgtgggcc aatgccgcca aatatgtcgt tatcggcggc ctgctcgggc    6360
gcctctcacc ccgccgcgcg gcgcgctgga acgcgctgcg cgatgcctgg agcatcgtgt    6420
tcggccagcc gcggcgctgg tggcacggct ggcgcgacca cgttcgtact tgaggatagc    6480
gccgcgccag acgcccgaaa atggcaaccc gacgcaaggc ggaaggcttg ccgacggcaa    6540 gcccccgac ttgtcgctca ctgcgcggcg ttgggcgccg gagcaggggc cgcagcaggc    6600
gcggcggcag cgccgccctg cagttgcggc ggcgggctgt agcccggctg atatttcacc    6660
gactcgcgcg ccttcttcag acgatcgttc agctgcgcgt ccgccgcctt gctgaaccgc    6720
tcggtgcgca gcgtattgag cgcgagttcg cgcgcctgat cgcccgccag cggctggatc    6780
gtcgtgccgg tgatgacatt ggcggtgacg ccctgctgcg tcggcaggat gaacagctcc    6840
tgcgccggca gcgccgcaat cttggcggcg atctccggcg gcaacgcggc ggtgtccagc    6900
tgggtcggcg cgcggcggaa ctgcacgccg tcggcggtca gcttggcggc aagctggtcc    6960
aacgtcttga gcgcgcgaa ttccttgaac ttcgccgccg agccgggcgg cgggaagacg    7020
atctgttcga tgctgtagat cttgcgctgc gcgaagcgat cgggatgcgc gcttcatat    7080 tgcgcgatct cggcatcggt cggctgggcg atgccgccgg caatcttgtc gcgcagcagc    7140
gtggtgagga tcaactcgtc ggcgcggcgc tgctggatca ggaagacggg ggtcttgtcc    7200
agcttctgct cgcgggcgta cttcgcgaga atcttgcgct cgatgatgcg ctgcagcgcc    7260
atctgctcgg caagcttgcg gtcggtcccc tgcggcacct gcgtggcctg cacttcggca    7320
ttcagttcga agatggtgat ctcgtcgccg tccacgctgg cgacgacctg cccttatcg    7380 agcttgcctt ccttgctgcc acatccggag acggccagcg cggccgcagc caccgccgtt    7440
accaggtaca atttcttcat gaagacctcc cagccggcac ggaattgcgc acggcacaaa    7500
cttctacttg aacctattcg ggcgggcggg catccgcaat agcgttggca gtgcagcatg    7560
cctcccggcg ggaggcaggc gggatcaatg ggggacggca tggcagaagc gacggtgacc    7620
gaagcgaagg cgggcaaacc gctgaaaatg tgtctcgcag cttccggcgg cggccatctg    7680
cggcagatcc tcgatctgga atcggtctgg aaggaacatg actatttctt cgtgaccgaa    7740
gacaccgcgc tgggccgcag ccttgccgaa aaacactcgg tcgcgcttgt cgatcactat    7800
gccctcggcc aggccaagct cggccacccg ctgcgcatgc tgggaggcgc ctggcggaac    7860
```

```
ctgcggcaga gcctgtcgat catccgcaag cacaagcccg atgtggtgat ctccaccggt   7920
gcgggcgcgg tctatttcac ggcgctgctc gccaagctct cgggcgcaaa gttcgtccac   7980
atcgaaagct cgcccggtt cgatcatcct tccgccttcg caagatggt caagggcatc    8040 gcgaccgtga ccatcgtcca gtccgccgcg ctcaagcaga cctggccgga tgcggagctg   8100
ttcgatccct tccgcctgct cgacaccccc cgccctccca agcaggcact caccttcgcc   8160
accgtcggtg ccaccctgcc ctttccgcgg ctcgtgcagg ccgtgctcga tctcaagcgg   8220
gccggcgggc tgccgggcaa gctggtgctg caatatggcg accaggacct ggccgacccc   8280
ggcatccccg acgtggagat ccgccggacc attcccttcg acgacctcca gctgctgctg   8340
cgcgacgcgg acatggtgat ctgccacggc ggcaccggat cgctggtcac cgcgctgcgc   8400
gccggctgcc gcgtcgtcgc cttcccgcgc cgccacgatc tgggcgagca ttatgacgat   8460
caccaggaag agatcgcgca gaccttcgcc gatcgcggcc tgctccacgc cgtgcgcgac   8520
gagcgcgaac tgggcgcggc agtggaggcc gccaaggcga ccgagccgca gctcgccacc   8580
accgatcaca cggcgctcgc cggccgcctg cgcgagttgc tggcacagtg gagtgccaag   8640
cgatgagcgc gccgcggatc agcgtcgtca tcccgcacta caatgatccg gactcgctgc   8700
gacaatgtct cgatgcactg cagcatcaga cgatcgggcg agaggccttc gagatcatcg   8760
tcggagacaa caactccccc tgcggcctgg cggcagtgga agccgccgta gccgggcgcg   8820
cgcggatcgt cacgatcctg gagaagggcg ccggaccggc gcggaacggc gccgcggcgg   8880
aagcgcaggg cgagattctc gccttcaccg acagcgactg cgtcgtcgag cccggctggc   8940
tggccggggg cgtcgcccat gtcgcccgg gccgcttcgt cggcggccac atgtatgtgc    9000
tcaagccgga agggcgactg accggcgcgg aagcactcga gatggcgctg gccttcgaca   9060
atgaaggcta tgttcgccgt gcgaagttca ccgtcactgc caatctgttc gtcatgcggg   9120
ccgatttcga gcgcgtcggc ggatttcgta ccggagtctc ggaagatctg gaatggtgcc   9180
accgcgccat cgccacgggt ctcgcgatcg actacgcccc cgaggcctcg gtaggccacc   9240
cgccccggcc ggactgggca acgctactgg tcaagacgcg gcgcatccag cgcgagctgt   9300
tcctgttcaa tatcgagcgc ccgcgcggcc ggctgcgctg gcttgcgcgc tcgacgctgc   9360
agcctgcgct gattccggcg gataccgcca agatcctgcg cacgcccggc acccgcgggt   9420
cccgtatagc tgccgtcggc acgcttgtcc gcctgcgctt ctggcgcgct ggcgccggcc   9480
tcctgcaact gctcggcaga ccaatctgat gaaggcgggg cggccatggt gcggcgcccc   9540
gtctcctgtc ctcacaccgc cgcgagcgcc tcttccagcg tcccgctgtc gatccgcagg   9600
cgtcccacca tcagccagag atagacgggc agcgaatcgt cgttgaagcg gaagcggcgc   9660
tccccgtcct gcgcatcgct ctccaggccg agctggcggc tcagcgcgtc gagttcctgc   9720
tcgacctgcg ccgcagtgat cgtgctcccc ggcagcagct cgacgactgc ctggccggtg   9780
aaccaaccat cggtcgaacg cgacgcctcg cccagcgcgg cgaccagcgg atcgtagcga   9840
ccgccgacga acttgcgcat ctccagcacg gcgcgcggcc acatccggcc ttctatttcc   9900
aggatggcct ggtcgagcgc gcggcgcaga tgcccagat cgacggtcag ccgcccctgg    9960
tcgagcgcct cgagcgccgc atggtggcac agcagccgcg cgaaataggg cgaccccagc   10020
gccagcaggt ggatgatccg ggtgaggttc ggatcgaagc gcaggcccga ggcggtctcg   10080
ccgagcgcga tcatctcctg tacctcggtt tcctcgagcc gcggcatcgg caggccgatg   10140
atgttgcggc ggatcgaggg tacgtagccg acgagttcct gcaggttcga cgagacgccg   10200
```

-continued

```
gcgatcacca gctgtacgcg cgcggagcgg tccgagaggt tcttgatcag ttcggcgacc      10260
tgctggcgga accgggtatc cgtcacgcgg tcatattcgt cgaggatgat cagaacgcgg      10320
gtgccggtga tgtcggcgca cagatcggcg agttcgcccg aatcgaacga tccggtcggc      10380
aggcgatcgg cgaggcttcc gcccgattcc gcctcgcccg cattgggcga gacgccgcga      10440
tggaacagca gcggcacatc ctctagcacc gcgcggaaca ggtcggcgaa gttggcattg      10500
gcgccgcagg tcgcgtagct gacgatgtag ctggattcac gcgccacgtc ggtcagcaca      10560
tggagcagcg aggtcttgcc gatgccgcgc tcgccataga gcacgacatg gctgcgctgg      10620
ctctcgatcg ccgagatcag ccgcgccagc acctcgaggc gaccggcaaa gctcgagcgg      10680
tccgccaccg gctgggtggg cgtgaagaag gtggcgagcg caaccgcgc gcgggtgatc        10740 tcgcgacgct cttcccggcg ccggtcgagc gggcgatcga gcgcggaagc gcgaaaggtc      10800
ggaaagtcgg gtcgcccgcg gcccgcatgc gcgtcgcgat ggggaacgac ggtggcggcc      10860
agcgggaaat atccgtcctc ctccggtacg tcccgacgcc caaagggcca caagaacttc      10920
agcgcggatc ctacagccac tcgaacacct cttaatttcg gacgccgcca cgctcggcag      10980
cgaacccctg gttcgcgcct tctggcgcct ccccaaacg atccggcccc gcctgtatca        11040
gcggcgcttg aaaaactcgt acggtttgat cacgaacgca atgtacgcca gcaccaatac      11100
aatcgtgagg attgcgaaaa catgatagtt ttcgttcccg agataattgg cgacggcaca      11160
tccgaccgcg ggaggcaaat agctgatcat cgtgtcgcgc actaccgaat ccgcctggga      11220
tcgttgcaag aagatcacga tcaggccggc gaatatcgcg atggtcaccc aatcataggg      11280
cgtctgcatg catgtccttt cttttcggcg ccggaatcga aggacttccg acgtcgcccg      11340
aaccgcacta gcagcggacg gtgcaactcg ctagataccg cggtgcagga taaaagctcg      11400
ttaaaacgcg accctaggaa tagcgcggta gcgccggcat gcgagaggtc gggcatgcgg      11460
aaggccgaag cggccgggac agcaccggat gggaggatat tcccgtagtg ggagtggcga      11520
ggccatggca tcctcagatc cggttgcttg tactggaggc cattgataat gaagccagga      11580
cccgggggaa cattcgtgcc agtaaaagac gttcagcaag cggtagaagt gcgcctcggc      11640
gatcgtgtct cgcgatcgtg ccgcgtgctc gcgctgcttg cgacggcaac ggcgatccag      11700
cccgcgctcg cgcagcgaca ggcgttcacg ccacgcccga gcggcagcga gcgccagatc      11760
agcgtgcatg caacgggaca gctcgagtac aacgacaatg tcgtgctcaa cgacccgcgc      11820
atcaccagcg gcgcgcgcgg cgacgtgatc gcctcccct ccctcgatct gagcattgtc        11880
ctgccgcgcg cgaccggaca gctctatctc gcgggcacgg tgggctatcg cttctatcgt      11940
cgctacacga acttcaatcg cgagaatatc tcgctcaccg gcggcggcga ccagcggatc      12000
gcgtcctgcg tggtgcatgg cgaagtcggc tatcagcgcc acctgacgga cctgtccagc      12060
gtcctcgtcc aggatactgc gcccgcgctc aacaacacgg aagaagcgcg cgcctattcc      12120
gcggacatcg gctgcgggtc cgcctacggc ctgcgccctg cacttgccta ttcgcgcaac      12180
gaggttcgca acagcctcgc ccagcgcaag ttcgccgatt ccgacaccaa cacggtcact      12240
gcccagttgg gcctgacgtc gccggcgctg gcaccgtgt cggtgtttgg acgcatgtcc        12300
gacagcagct acatccatcg cacggtaccg ggggtcagtg gccgcgacgg catgaagagc      12360
tatgcggccg gcgtccagct cgagcgggcg gtctccagcc ggctgaattt ccgcggctcc      12420
gtcaattatt cggaggtcga ccccaagctc gcctcgacgc cgggcttcag cgggatcgga      12480
ttcgatctgt cggcggtata ttcgggcgat caatatggcg tgcagctcct tgcgtcgcgc      12540
aacccgcagc cctccacgct gctgttcgta ggctatgaaa ttgtgacgac cgtgtcggca      12600
```

```
acggcaaccc gtaagctgag cgatcggacc caactctcgc tacaggccac caagacctgg    12660
cgcgagcttg cctcttcgcg gttgttcact cttgcgccga cgacgggcaa cgacaacacg    12720
ctgacgctgt tcggcaccgt gaacttccga cccaatcctc ggctgaactt ctcgctgggt    12780
gcgggctata acaagcgcac cagcaatatt gggctgtatc aataccgctc caaacgtatc    12840
aatctcacga cgtcgctgtc gctctgacaa gggccgtatt catgcatgac aaacaccgtt    12900
tcgtgatcct ttcggcgctc accggaattg ccgtactcgc cgcgcccgcg gcagcgcaga    12960
ttcccacccg gtccgttccg acgccggcgc gggcgcgccc ggcgaccccg ccagcggccc    13020
cgcagcagca gacgacggca gtgccgacaa cggcagccac cgccaccccg ccggctgcgg    13080
gtgcggcgcc ggccggctac aagatcggcg tcgacgacgt gatcgaggcg gacgttctgg    13140
gccagtcgga cttcaagacc cgcgcgcgcg tgcaagcgga cggtaccgtc acccttccct    13200
atctcggcgc cgtgcaggta cggggcgaga ccgccgtcac gctggccgag aagctcgccg    13260
gcctgctgcg cgcgggtggc tattacgcga agccgatcgt cagcgtcgaa gtcgtcagct    13320
tcgtcagcaa ctatgtgacg gtgctgggcc aggtgaccac ggccggcctg cagccggtgg    13380
atcgcggcta tcacgtctcg gagatcatcg cgcgcgccgg cggccttcgc gccgatgcgg    13440
ccgatttcgt ggtgctcacc cgcgccgacg gcaccagtgc caagctgaac tacaagcagc    13500
tggcccaggg cggcccggag caggatccgg tggtcacgcc tggcgacaag ctgttcgtgc    13560
cggaagtcga gcacttctac atttatggcc aagttaacgc gcctggggta tacgcgattc    13620
gaacggacat gacgctccgt cgcgcgctgg cacaaggcgg cggccttacc cccgccggct    13680
cgtcgaagcg agtgaaggtc tcgcgcgacg gccaggaaat caagttgaag atggacgatc    13740
cgatcaagcc tggcgacacg atcgtcatcg gcgagcggtt gttctgatct aggcaatgtt    13800
gacagcggac gaggcccacc agtgaatatc attcagttct ccgcattct ctgggtgcgc    13860 cggtggatca tcctcccggc gtttctcgtc tgcgtcacca ccgcggcgct ggtggtccag    13920
ttcctgcccg aacgctaccg cgcgaccacg cggctggtgc tcgacacctt caagcccgat    13980
cccgtcaccg gccaggtgat gaactcgcag ttcatgcgcg cctatgtcca gacgcagacc    14040
gagctgatcg aggactatgc gacctccggc cgcgtggtcg acgaactggg ctgggccaac    14100
gatcctgcca acatcgctgc cttcaacgcc tcgtcctcgg cggcgaccgg cgacattcgc    14160
cgctggctcg caaagcagat ctcggacaac accaaggcgg atgtgatcga gggcagcaac    14220
atcctcgaaa tctcctactc ggacagctcg cccgagcgtg ccgagcgtat cgccaacctg    14280
atccgcaccg cattcctcgc ccagtcgctc gccgccaagc gccaggcggc ggcgaagtcg    14340
gccgactggt acacccagca agcggaagcg gcacgccagt cgctgctcgc ggcggtgcag    14400
gcgcgcaccg acttcgtgaa gaagtccggc atcgtgctga ccgagaccgg ttcggatctc    14460
gatacgcaga agctcgcaca gctccagggc gcgagcgcga taccgtcggc accggtcgtc    14520
gcggccgcca gcggcatggg cccggcgcag ctccagcttg cccagatcga ccagcagatc    14580
cagcaggcgg ccaccaatct cggcccgaac cacccggcct tccaggccct gcagcgccag    14640
cgcgaggtgc tcgcccgcgc agcggcggcg gaacgcagcc aggcaagcgc cagcggcccc    14700
ggccgcggcc cgctggaaag cgaagccaat gccagcgcg cccgcgtgct cggcaaccgc    14760
caggatgtcg acaaggtcat gcagctccag cgggacgtca cgctgaagca ggaccagtat    14820
atgaaggcgg cccagcgcgt cgccgatctg cgcctggaag caagcagcaa cgacacgggc    14880
atgagcacgc tgagcgaagc cagcgcgccg gaaacgccct attaccccaa ggtgccgatg    14940
```

```
atcatcggcg gcgcggccgg cttcggcctc ggcctcggcg tgctggtcgc gctgctcgtc      15000
gaactgctcg gtcgccgcgt gcgcagcgcc gaggatctcg aagtggcggt cgatgcgccg      15060
gtgctgggcg tgatccagag ccgtgcctcg ctcgccgcac gcctgcgccg cgcccaagaa      15120
accctcggcg accgcgccga aacgcacgga gcttcagtaa actgatggac gcgatgacca      15180
gcgaaccgct gcccgaaggc gagcgcccga gcgccgttcc gacgacgccc gacaccaccg      15240
gcgtcctgga atatcagctc gtcctgtccg acccgaacgg catcgaagcg gaagccattc      15300
gcgcgctgcg caccegcatc atggcgcagc acctgcgcga gggccgccgc gccctggcga      15360
tctgcggcgc ctcggccggc gtcggctgca gcttcaccgc cgccaacctc gcgacggcgc      15420
tggcgcagat cggcatcaag accgcgctgg tcgatgccaa tctgcgcgac ccgagcatcg      15480
gcagcgcctt caacatcgcc gccgacaagc cgggcctcgc cgactatctc gcctcgggcg      15540
atatcgacct cgcctcgatc atccacccga ccaagctgga ccagctgtcg gtgatccatg      15600
ccgggcatgt cgagcacagc ccgcaggaac tgctgtcctc cgagcagttc cacgacctcg      15660
tgacgcagct gctgcgcgag ttcgacatca cgatcttcga caccacggcc gcgaacacct      15720
gcgccgatgc gcagcgcgtc gcacatgtcg ccggctatgc gatcatcgtg gggcggaagg      15780
attcgagcta catccgcgac gtcaacacgc tcacccgcac gctgcggtcg gaccgcacca      15840
acgtcatcgg ctgcgtcctg aacggctatt gaattggatt ccatgaccgc gactgcgctg      15900
gagcggcagc aaggacggcg acagggggggc tattggctcg cggtcgccgg ccttgcggca      15960
ctcgccattc ccactttcgt cacgctcggc cgcgaaacct ggagcgccga aggtggcgtg      16020
caggggccga tcgtgctggc gaccggcgcc tggatgctgg cgcggcaacg cgacagcctc      16080
gtggcgctcc ggcgccccgg caatctggcg ctgggcgcat tgtgcctgtt gctggcgctg      16140
ggcatctaca ccgtcggtcg cgtgttcgac ttcatcagca tcgagacgtt cgggctggtc      16200
gcgaccttcg tggcggctgc gttcctctat ttcggcggcc gggcgctgcg cgctgcgtgg      16260
ttcccgacct tgtggctgtt cttcctcgtg ccgccgccgg gctggatcgt cgatcgcgtc      16320
accgcgccgc tcaaggagtt cgtctcctat gccgccaccg gcttcctgtc ctggctggac      16380
tatccgatcc tgcgccaggg cgtgacgctg ttcgtcggcc cctatcagct gctggtcgag      16440
gatgcctgtt cggggctgcg ctcgctctcc agcctcgtcg tcgtcacgct gctgtacatc      16500
tacatcaaga acaagccgtc ctggcgctac gcgctgttca tcgccgcgct ggtgatcccg      16560
gtcgcggtga tcaccaacat cctgcgcatc gtcatcctcg tgctgatcac ctatcatatg      16620
ggcgacgagg ccgcgcagag cttcctccac gtctccaccg gcatggtgat gttcgtggtc      16680
gcgctgctct gcatcttcgc catcgactgg gtggtcgaac agctcttcac acggcgccgg      16740
aggccccatg ttcaaccggc gtgacctgct gatcggcgcg ggctgcttcg ccgccgccgg      16800
cgcctcgctc ggcctcaagc cgcaccgtcg catggacctg ctcggtgcga ccaagctcga      16860
tgcgctgatg cccaaggcat tggcggctg gaaggccgag gataccggtg cgctgatcgc      16920
ccccgcgcgc gaaggcagcc tggaagacaa gctgtacaac caggtggtcg cccgtgcctt      16980
ttcgcgcgcc gacggcaccc aggtgatgct gctgatcgcc tatggcaacg cccagacgga      17040
tctgctgcag ctccaccgac cggaagtctg ctacccgttc ttcggcttca ccgtggtcga      17100
gagccacgag cagatcatcc cggtgacgcc gcaggtgacg attcccggac gggcgctgac      17160
cgcgaccaac ttcaaccgca ccgagcagat cctctactgg accccgcgtgg gcgaatatct      17220 gccgcagaac ggcaacgagc agctgttcgc ccgcctcaag agccagctcc agggctggat      17280
cgtcgacggg gtgctggtcc gcatctcgac tgtgacggcg gaagccaagg acggcctcaa      17340
```

-continued

```
cgccaatctc gatttcgcgc gcgagctggt gaagacgctc gatccgcgcg tgctgcgccc    17400
gttgctcggc acgcaggtaa cgcgcgacct ggcgccgcgc gcctgaacga aaaaggggcg    17460
gcgcagaccg ccgcccctcc ctctccttct cgtcgcgtac ccgcgctcag cgctcgtgca    17520
gcgcgtcgct gccggtttcg agcatcgggc cgacgagata gctcagcaat gtccgcttgc    17580
cggtgacgat gtcggcactg gcgatcatgc ccggccgcag cggcacgtgc ccgccattgg    17640
cgatgacata gccgcggtcc agtgcgatcc gcgccttgta gaccggcggc tggccctcct    17700
tcacctgcac cgcctcgggc gcgatgccca ccaccgtgcc ggggatcatg ccatagcggg    17760
tgtgcgggaa cgcctgcagc ttcacccttta ccggcatgcc ggtgcgcacg aagccgatat    17820
cgctgttgtc caccatcacc tcggcctcga gccgggcatt gtccggcacc agcgacagca    17880
gcggcttggc gccctccacc acgccgcctt cggtgtggac ctgcagctgc gagaccgtgc    17940
cgctgaccgg cgcgcgcagt tcgcggaacg aactgcgcag attcgccttg gcgacttcct    18000
cgctgcgcgc ccgcacgtcg tcctgcgcct tcaccagatc ctgcaacacc tgcgcgcgcg    18060
cctcctcgcg cgtcctgatc gacatgctgc tggcactgcg cgactgctga ccaagcttgg    18120
ccaccgtcgc ccgcgccgcg gtgaggtcct gccgttcgga aatgagctgg cggcgcatct    18180
cgaccacgcg cagcttcgag acatagccct tggcggccat cgcctcgttc gcggcgatct    18240
gctgctcgag cagcggcagc gattgttcca gcttgcgaac ctgcgcctgt gcctcggccg    18300
aggcggaagc ggcggcaccg ctgtccgatc ggccgccggc aagcatcgcc tcgatctggc    18360
cgagccgcgc gcgtgcgagg ccgcgatgcg tctcgacctc cgcggcgcct gcggcggcgg    18420
gcgcggcgaa gcggaagccc tttccgtcca gcgcgtcgat gatcgcctgg ttgcgcgcgg    18480
catcgagctg ggcgctgagc agcgccacgc gcgcctgcgc ggcttcggct gccgacatgg    18540
tgggatcgag cgtgatcagc acctggccct tctgaacctt ctgccctcg cccaccagaa    18600 tgcgccggac gataccgctt cgggggact gcacgatctt ggtctcgccg atcggggcga    18660
tgcggccctg cgtcggcgcc accacttcca cgcggccgat tgccagccag gcggtggtga    18720
tcgccagccc cgccaccatc acccggccgg tgaggcgcgc ggtgggcgac accggacgtt    18780
cgatgatctc gagcgcggcc ggcaggaatt cggtatcata ggcatcggcg cgagcgggca    18840
gcacggtgcc gcgcatgcgg gcgatcgggc cgccgcggcc gatcggaaca acggcgttca    18900
tgcggcaatc tccccatatc cgctttggcg gcggtgcagg tcggcatagc ggccgcccaa    18960
gcgtagcagt tcgtcatgcc ggccgctctc gacgatgcgc ccctgctcca gcgtgatgat    19020
ccgatcgcag gcgcgtaccg cggacaggcg gtgggcgatg atcaccagcg tgcggcccgc    19080
cgagatggcg cgcagattgt tctggatcag ctcctcgctc tcggcatcca gcgcggaggt    19140
cgcctcgtcg aacaccagga tgcgcggatt gccgaccagc gcgcgggcga tagcgagccg    19200
ctggcgctgg ccgcccgaca ggttgacgcc gcgctcgacg atctcggtgt catagccgcg    19260
cggctgacgc aggatgaagt catgcgcacc cgccagcgtc gccgccgcca cgacatgctc    19320
gaacggcatc gccgggttgg acagcgcaat gttctcgcgg atcgagcggc tgaacagcag    19380
attttcctgc agcacgacgc cgatctgccg gcgcagccag gcgggatcga gctgggccac    19440
atccacctcg tcgaccagca cgcggcccag atcggggtg ttgaggcgct gcagcagctt    19500
ggccagcgtc gacttgcccg accccgagga gccgacgatg ccgagcgacg tgccggcggg    19560
gatgtcgagc gtgatgtcgc tcagcaccgg cggctggtcc tcggcatagc ggaaggtcac    19620
gttttcgaag cggatcgcgc cgcgcagcac cggcagcgtc gcggcggagg ccggccgcgg    19680
```

-continued

| | |
|---|---|
| ctccaccgga tggttgagca cgtcgccgag gcgctcgatc gcgatgcgga cctgctggaa | 19740 |
| gtcctgccac agctgggcca tgcggatcac ggggccggaa acgcgctggg cgaacatgtt | 19800 |
| gaacgccacg agcgcgccga cgctcatcgc gccaccgatc acggccttgg cgccgaagaa | 19860 |
| caggatcgcc gcgaagctca gcttggagat cagctcgatc gcctggctgc cggtgttggc | 19920 |
| gacgttgatc agccgctgcg acgaggcggt ataggcggcg agctgacgtt cccagcgatt | 19980 |
| ctgccagtgc ggttcgactg cggtcgcctt gatggtgtgg atgccggaga cgctctcgac | 20040 |
| gagcagcgcg ttgctggcgg agctcttctc gaacttgtcc tcgacacgcg tgcgcagcgg | 20100 |
| gcccgcgacg ccgaacgaga ccatcgcata ggcgaccagc gacacgatca cgacgccgaa | 20160 |
| cagcatcggc gagtagaaca gcatcgcgcc gaggaacacg accgtgaaca gcggatcgac | 20220 |
| catcaccgtc agcgacgcat tggtgaggaa ttcccggatg gtctcgagct ggcggacccg | 20280 |
| ggtgacggtg tcgcccaccc gccgcttttc gaaatagccg agcggcagcg ccagcagatg | 20340 |
| gtggaacagc cgcgcgccca gctcgacgtc gatcttctgc gtcgtctcgg tgaacaggcg | 20400 |
| cgtgcggatc cagcccagcg ccacctccca gaccgacacg gccaggaagg cgaaggcgag | 20460 |
| cacgctcagc gtgctcatgc tgttgtggac cagcaccttg tcgatcacgc tctggaagag | 20520 |
| cagcggcgcc gcgaggccga gcaggttgag cgccagggtg atgcccagca cctcgagaaa | 20580 |
| cagcctgcga taccgctgga actgtgcggc gaaccaggag aaaccgaatc gcagcgcctg | 20640 |
| gccggccacg gcgcgcgtcg tcagcagcac gagcgtgccg gaccacagcg catccagccc | 20700 |
| ctcgcggtcg acctgttcgg gggcgtggcc gggacgctgg atgatcacgc catgctcggt | 20760 |
| caggccaccg atcacgaacc agccctccgg gccgtcggcg atggccggca gcggctggcg | 20820 |
| ggccagaccg ccgcgcggca cgtccaccgc cttggcgcgc acgccctgct ggcgcttggc | 20880 |
| gagcaggatc aggtcgtcga cgctggcacc ctcggcatgg cccagcatgt gccgcagctg | 20940 |
| ttcggggtg acgcgatgt tgtggacgcc gagcagcagc gacagcgcca caagcccgga | 21000 |
| ttcgcgcaat tcgccctcgc gctcggcggc agcctgggcg gcgaacgcgc cctggagctg | 21060 |
| tgcctgcatc tcgtcgcgtg tcattccggt actctgcctc catggcgcta ctgatcgcag | 21120 |
| ccatgatgaa cgagctcggt aaagactcgc ttaagccaga ttttctgtg gtttatacct | 21180 |
| attgccgggg atgccggacc ggaccggatc ggcagacggc agcctgcgtt agtcgggcct | 21240 |
| taaagcgttg ccgctagcac aaggacaaga attttatcgg agagggtcgg gaaccatgcc | 21300 |
| cacgcatgaa ggttgcagcg cagcaatatc gacggatcgc ctcggagccc gaatgctgca | 21360 |
| tccgcgaagt gactttcgcc aaagcagcta taggatggcc cggggcttga ttgccgccgt | 21420 |
| gcgatcagca taagcgatcc atggtcgcca aaatctgtca tccttggtaa caatcatgca | 21480 |
| gccgctaagg aagatgtgca cgtctgacga tgctttcttc cgcaccccat gcgccgctga | 21540 |
| ctctggtaga ttgaccgtgg cctccattgc tcatcgtctc gaaaaaggac cctctggtcg | 21600 |
| ccgcgcggac ttccgggaat cgatttgtcc cgttatagtg caatgcaaca ggccgaatcg | 21660 |
| gccgctgtca gcgtgcacaa tccgttgagg gagcccgacg aggcaatgaa cgcttttgaa | 21720 |
| gcacagcgcg ccttttgagga gcagctccgg gcccatgccc gttctgcccc cagcgccgca | 21780 |
| cccatgctgc gacgttccac gatccgcatg atcctctaca ccgaattgct gttgctcgac | 21840 |
| agcatcgcaa ttctactggg gttctacatc gcggcctgct cgcgcgacgg caactggctg | 21900 |
| tcccttgcgg gcgtcaatgt cggcatcttc ctcctgccga tcacgctcgg caccgcgctc | 21960 |
| gccagcggca cctattcgct gagctgcctg cgctacccgt cagcggggt gaagagcatc | 22020 |
| ttctcggcgt tcttcttctc ggtgttcatc gtgctgctgg gcagctacct gctcaccgcg | 22080 |

```
gagctgccgc tgtcgcgcct gcagctcggc gagggcgtgc tcctggcgct cagcctggtg    22140
acgatctgcc gccttggctt ccgctggcac gttcgtgcgc tgacacgcgg cacgctgctc    22200
gacgagctgg tgatcgtcga cggcgttgcc ctggaggtcg cgagcggcgc ggtcgcgctc    22260
gatgcgcgca tcatcaacct cacgcccaac ccgcgcgatc cgcagatgct gcatcgcctc    22320
ggcaccaccg tggtgggctt cgaccgggtc gtcgtcgcct gcaccgagga gcaccgggca    22380
gtatgggcgc tgctgctcaa gggcatgaac atcaagggcg agatcctcgt cccccagttc    22440
aacgcgctgg gcgcgatcgg cgtcgactcc tatgagggca aggacacgct ggtcgtgtcc    22500
cagggcccgc tcaacatgcc gaaccgcgca agaagcggg cgctcgatct gctcatcacc    22560
gtccccgcgc tggtcgcgct ggcgccgctg atgatcgtgg tcgcgatcct gatcaagctg    22620
gagagccccg gccccgtctt cttcgcacag gaccgcgtcg gccgcggcaa ccgactgttc    22680
aagatcctca agttccgctc gatgcgcgtt gcgctctgcg atgcgaacgg caacgtctcg    22740
gccagccgcg atgacgatcg catcaccaag gtaggccgga tcatccgcaa gaccagcatc    22800
gacgagctgc cgcagctgct caacgtgctg cgcggcgaca tgagcgtcgt cggcccgcgc    22860
ccgcacgcac tcgggtcgcg cgccgccaac catctcttct gggaaatcga cgagcgctac    22920
tggcaccgcc acacgctcaa gccgggcatg acgggcctcg cgcagatccg cggcttccgc    22980
ggcgcgaccg atcgccgcgt cgatctcacc aatcgcctgc aggcggacat ggagtatatc    23040
gacggctggg acatctggcg ggacgtcacc atcctgttca agacgctgcg cgtgatcgtg    23100
cactccaacg ccttctgatc gcggagggga gcaacgcgag caccgcttgg tgcaagagca    23160
ttgacatccg ccctgcttct gcatttgtca ttttatcatt gtcgttgcgg gcccgcccgc    23220
gccatggggg attttgaatg aagggtatca tccttgcggg gggcagcggc acgcgcctct    23280
accccgcaac gctgtcgatc tcgaagcagc tgcttcccgt ctatgacaag ccgatgatct    23340 tctacccct gtcggtgctg atgctcacgg gtatccggga catcctgatc atctccaccc    23400
cgcgcgacct gccgatgttc caggcgctgc tcggcgacgg ttcggcattc ggcatcaacc    23460
tgagctatgc cgaacagcct tcgcccaacg gccttgcgga agccttcatc atcggcgccg    23520
atttcgtcgg caacgatccc agcgcgctga tcctcggcga caacatctat acggtgaaa    23580 agatgggcga gcgctgccag gcagctgcgg cccaggcatc gcagggcggc gcgaacgtgt    23640
tcgcctatca tgtcgacgat cccgagcgct acggcgtggt cgcgttcgat ccggagacgg    23700
gcgtcgctac cagcgtcgag gaaaagccgg ccaacccaa gtccaattgg gcgatcaccg    23760
ggctttattt ctacgacaag gacgtggtcg acatcgccaa gtcgatccag ccctcggcgc    23820
gcggcgaact cgagatcacc gacgtcaacc gcatctacat ggagcgcggc gacctccaca    23880
tcacccggct cggtcgcggc tatgcctggc tcgacaccgg cacgcatgac agcctgcacg    23940
aggccggctc gttcgtccgc acgctggagc accgcaccg cgtgaagatc gcctgccgg    24000 aggaaatcgc cttcgagagc ggctggctgg gcgccgacga tctgctcaag cgcgccgccg    24060
gcctcggcaa gacggggtat gccgcctatc tgcgcaagct ggtagccgcg gcatgaccca    24120
ggtgcatcac cacgcgctat cgggcgtcat cgagttcacc ccgcccaagt acggcgatca    24180
ccgcggcttc ttctccgagg tgttcaagca gtccacgctc gacgccgaag gcgtcgaggc    24240
gcggtgggtg caggacaatc agagcttctc ggccgcaccg ggcacgatcc gcggactgca    24300
cctgcaggcc ccgcccttcg cccaggccaa gctggtgcgc gtgctgcgcg gcgcgatcta    24360
cgacgtcgcg gtcgacattc gccgcggctc gcccacatac ggccagtggg tcggcgtcga    24420
```

-continued

```
gctttcggcg gacaagtgga accagctgct ggtgccggcc ggctatgcgc atggcttcat    24480
gacgctcgtc ccggattgcg agatcctcta caaggtcagc gccaaatatt cgaaggaatc    24540
ggagatggcg atccgctggg atgatcccga tctcgccatc acctggccgg acatcggcgt    24600
cgagccggtg ctctccgaaa aggacgcggt cgctaccccg ttcgccgaat tcaacacccc    24660
cttcttctat cagggctgat ccatgcagca gaccttcctc gttaccggcg cgcgcggctt    24720
catcggctcg gcagtggtac gccacctcgt tcgccagggc gcgcgcgtca tcaatctcga    24780
caagctcacc tatgcgggca acccggcctc gctgaccgcg atcgagaacg cccccaacta    24840
ccgcttcgtc cacgccgata tcgccgacac cgcgacgatc ctgccgctgc tgcgcgaaga    24900
gcaggtcgac gtggtgatgc acctcgccgc cgagagccat gtcgatcgct cgatcgacgg    24960
cccgggcgag ttcatcgaga ccaacgtcgt cggcaccttc aagctgctcc aggcggcgct    25020
gcaatattgg cgcgagctgg aaggggagaa gcgcgaggct ttccgcttcc accacatttc    25080
caccgacgag gtgttcggcg acctgccgtt cgacagcggc atcttcaccg aagagacgcc    25140
ctatgatccc tcctcgccct attcggcgtc gaaggcggcc agcgaccatc tggtccgcgc    25200
ctggggtcac acctatggcc tgcccgtggt gctgtcgaac tgctcgaaca attacgggcc    25260
gttccacttc cccgagaagc tgatcccgct gaccatcctc aacgcgctgg aaggcaagcc    25320
cctgcccgtc tacggcaagg gcgagaatat ccgcgactgg ctgtacgtcg acgatcacgc    25380
caaggcgctg gcgacgatcg ccacgaccgg caaggtcggc cagagctaca atgtcggcgg    25440
ccgcaacgag cgcaccaacc tgcaggtcgt cgagacgatc tgcgacctgc tcgatcagcg    25500
cattccgctg aaggatggca agaagcgccg cgagctgatc accttcgtca ccgatcgccc    25560
cggccatgac cgccgctacg cgatcgacgc gaccaagctc gagaccgaac tgggctggaa    25620
ggccgaggag aatttcgaca ccggcatcgc cgcgacgatc gactggtatc tcgagaatga    25680
atggtggtgg ggtccgatcc gctccggcaa atatgccggc gagcggttgg ggcagaccgc    25740
ctgatgcgca tcctcgtcac cgggcatgac ggccaggtcg cccaggcgct gggcgaacag    25800
gcggagggcc atgagctgat cttcaccagc tatcccgagt tcgatctctc caagccggag    25860
acgatcgagg cggcggtggc gaagatccag cccgagctga tcgtgtcggc ggctgcgtat    25920
acggcggtcg acaagtccga gagcgagccc gagctcgcca tggcgatcaa cggcgacggc    25980
cccggcgtac tggcgcgcgc gggcgcgaag atcggcgcgc cgatcatcca tctgtcgacc    26040
gactatgtgt tcgacggcag cctggaccgc ccgtggcgcg aagacgaccc caccggtccg    26100
ctcggcgtct atggcgccac caagctggcc ggcgagcaag cggtgcaggc ctcgggcgcg    26160
accaacgcgg tgatccggct cgcctgggtc tacagcccgt tcggcaacaa cttcgtcaag    26220
acgatgctgc gcctcgccga gacgcgggac acgctgaacg tggtcgagga ccagcagggc    26280
tgcccgagct cggcgctgga catcgccacg gcgatcctca aggtcgtcgg ccactggcag    26340
cagaacggcg ccaccagcgg cctgtatcac ttcaccggat cgggcgagac caactgggcc    26400
gacttcgcgc gcgcgatctt cgcggaaagc gccaagcacg gcggtccgac cgccgaggtg    26460
accggcattc cgacctccgg ctaccccacc ccggcgaagc gcccggccaa ttcgcggctc    26520
aattgcgaca gttcgccga aaccttcggc tatcgtgcac ccgcctggca ggactcggtg    26580
gcggaagtgg taggccgcct cctggcataa aatgcccggc ccgaccctgt gcgcggcggg    26640
gtggctgcgc actccggtcg ggtttcatcg acatcgccgg ctgcggggag catcaccgat    26700
gctccccgat cagcgccagg ccgtcacttc ctgaacggcg cgaccagggg cttgatcgtc    26760
ttgaacacgg cctcacgcag cgtccgcacg ggcgcggcga cgaggtgatc gaacgcgagc    26820
```

```
                                                               -continued gtcatcccgc tcaccgctg gggtgcgacg tcgctgcgga tcttgaacga ttcgaccacc  26880
tcgatatcgg aaaccagccg ccccttgatg cggttgatga cattctcgcc atgcaccacc  26940
tgcagccata ccggccgccc ggcgacctgg gtgatcttcc acttctggcc cagctcatga  27000
tggggcttgg cccagatcgt ctcgacgctg gcgagatcgc gctcgaccag cgaggtgaac  27060
ggattgctgt ggtccgcagc ggtgtagagc cggccctggc gcatcgcgat gccctgggtg  27120
aagttcagca ccgtctgtgc cggcgcatcc ttcgccgcgg cctgcacccg tgccacgaag  27180
tcgttcgaaa gcgcgtcgtc attgtccagc cgcgtggtga cgatcagctg ctcgccgggc  27240
gtcgccagcg ccttcacgtc gtccgcgatc atcgccttgt cgaacatcgc gacgtagcgc  27300
ggcgtgaagt tgtagatctg ccgatcgcgc tcgatccgct cgcggaactc ggcggggggtg 27360 tccttgtcga agtagatgag ccagtggaag ttgcgctcgg tctggcccgc gatgctcggc  27420
aggcagaact gctcgaacag cccgaaacgg cggtcgagcc aacccggcga attgcggatc  27480
gccacctcgc ggcccgggct ggcgatgttg aagcgcgtca ggatcacgtg aagcatcggt  27540
tcgatcagcc ccggtctagc aaaacgaaga aagcccggcc gctacaacgg ccttgttcga  27600
acaacgcgca agaaacaggg tacacgcgaa cggcacgttc gtcttcgccc accccgctgg  27660
ttgccgccat tcccacgaac ggttacggga tattccggaa ctgggcaacc ggggattgct  27720
gcactgcgca atgacacgcg gccggaatga caaacggctt gccgcccgcg cccccgcgc   27780 ctaaccctcc gcccgtgccc gacgcccgtc ccgatcgcat tgccaccggc ctggcgcttc  27840
gcctgttcgc cattgcctgc ctgtcgacca tgtcggcgct catcaagatg tcggaactgc  27900
gcggcgcctc gctgatcgag acgatgttcc accgccagct ctgggcggtg ccgctggtca  27960
ccttgtgggt ggtgatgggc ccggggctca agtcgctcaa gacgcagcgc ttcggcgcgc  28020
atgtctggcg caccgcggtg ggcctcaccg gcatgatctt caccttcggc gcggtgatcc  28080
tgctgcccct ggccgaggcg cagaccttcc agttcaccgt gcccatcttc gccacgctgc  28140
tcggcgcgct gatcctcggc gagccgaccg gccggcatcg ctggggcgca gtgatcgtcg  28200
gcttcctcgg cgtgctgatc gtcgtccagc cgggccggga agccattccg atcttcggcg  28260 ccttgtcgg gctgatggcg gcgttgttcg tcgccatcgt cgcgatcacg ctgcggcaga  28320
tcacccgcac cgaaagcgcc ggcaccaccg tcttctggtt ctcgctgctc tcggtgcccg  28380
tgctcggcgc catctacgcg ttcaacttcc gtccgcacga tgccgagacc tgggcgatcc  28440
tcatcgccac aggactggtg ggcggcgtcg gccagctggc gctgaccggt gcgatgcgct  28500
tcgcccccgt ctcggcggtg gtaccgatgg actattcggg gctgatctgg gcgacgctct  28560
acggctggct gctgttcgac gtgttcccga ccttctcgac ctggctcggt gcgccggtga  28620
tcatcgccag cgggctctac atcgtctatc gcgagcagaa gctggcccgc ggccaggcta  28680
gctacgccga aacgccacta tgaggttgtt ggcgggcatc gccacccgcc gatcgaacac  28740
caggccttgc gcccccgccg ccgcgatcac ctcgtccagc aagcgcagcc cccaggcagg  28800
atcc                                                              28804
```

PRODUCTION OF NON-NATIVE BACTERIAL EXOPOLYSACCHARIDE IN A RECOMBINANT BACTERIAL HOST

This application claims benefit of U.S. provisional application 60/049,428, filed Jun. 12, 1997.

BACKGROUND OF THE INVENTION

Xanthan gum is an acidic exopolysaccharide (EPS) normally secreted by *X campestris* (Jeanes, A, et al., 1961, J Appl Polymer Sci 5: 519–526), and is useful as an aqueous rheological control agent because it exhibits high viscosity at low concentration, pseudoplasticity, and insensitivity to a wide range of temperature, pH, and electrolyte conditions (see U.S. Pat. Nos. 5,194,386, 5,472,870, 5,279,961, 5,338,841, and 5,340,743, the contents of each of which are incorporated herein by reference). The genes that code for its synthesis are gumB through M (Capage, Mass., et al., 1987, WO87/05938; Vanderslice, R W, et al., 1989, the contents of which are incorporated by reference; Genetic engineering of polysaccharide structure in *Xanthomonas campestris*. In: Biomedical and biotechnological advances in industrial polysaccharides, V Crescenzi, I C M Dea, S Paoletti, S S Stivala, and I W Sutherland, eds, pp 145–156, Gordon and Breach Science Publishers, New York).

A different source of commercially significant and functionally diverse biopolymers is the genus Sphingomonas (Pollock, T J, 1993, J Gen Microbiol 139: 1939–1945). Different organisms of this genus secrete a variety of different strain-specific exopolysaccharides For example, one species secretes Gellan®, while others secrete welan, rhamsan, S-88 or other polysaccharides (Moorhouse, R, 1987, Structure/property relationships of a family of microbial polysaccharides. In: Industrial polysaccharides: genetic engineering, structure/property relations and applications. M Yalpani, ed, pp 187–206, Elsevier Science Publishers B. V. Amsterdam).

We refer to this group of polymers as "sphingans," after the common genus, because they also have common carbohydrate backbone structures (-x-glucose-glucuronic acid-glucose-; where x is either L-rhamnose or L-mannose) with distinct side chains. (See U.S. patent Applications Ser. No. 08/592,874, filed Jan. 24, 1996, and Ser. No. 08/377,440, filed Jan. 24, 1995, the contents of each of which are hereby incorporated by reference). The structure for sphingan S-88 is shown in FIG. 1. The organization and DNA sequence of 23 genes (FIG. 2) that direct the synthesis of sphingan S-88 have been described (Yamazaki, M, et al., 1996, J Bacteriol 178: 2676–2687).

The commercial production of highly viscous xanthan gum and other bacterial polysaccharides is a complex biosynthetic and process-engineering problem (Kennedy, J F et al., 1984, Prog Industrial Microbiol 19: 319–371). The sugar substrate is important primarily because the sugar affects productivity, but the cost of the sugar can also be significant. Currently, xanthan gum is produced by supplying *X. campestris* with corn syrup, sucrose or starch. Yet, three to four typical cheese factories can provide enough low-value lactose-containing waste whey to satisfy all of the existing worldwide demand for xanthan production.

A recombinant strain that can stably convert lactose into xanthan gum in amounts equal to the conversion of glucose is disclosed in U.S. Pat. Nos. 5,434,078, and 5,279,961, the contents of each of which are incorporated herein by reference.

It is desired to improve the methods of the production of xanthan gum to achieve more cost-effectiveness, convenience, more desired product qualities and greater production efficiency.

A problem encountered with xanthan gum produced by conventional methods, is that it is contaminated with a cellulase which can be very disadvantageous in commercial applications where xanthan is mixed with or contacts cellulosic polymers. The result is deterioration of the cellulosic polymers.

Methods are known for the treatment of xanthan gum which has been separated from fermentation broths to remove the cellulase contaminant. However, these treatments require processing of the xanthan gum and add to the expense and overall complexity of the process.

SUMMARY OF THE INVENTION

Figure 1:
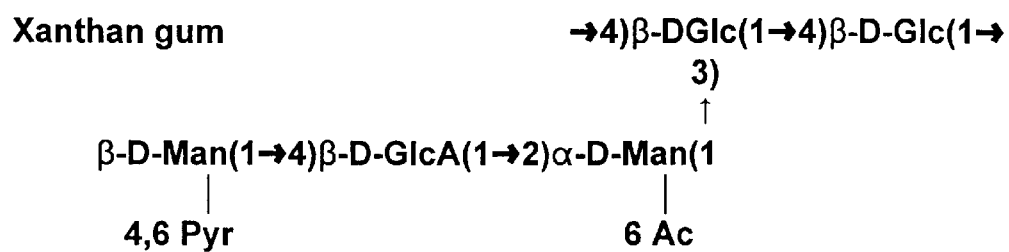
FIG. 1 shows the repeating subunit structures of xanthan gum and sphingan S-88.
Figure 1:
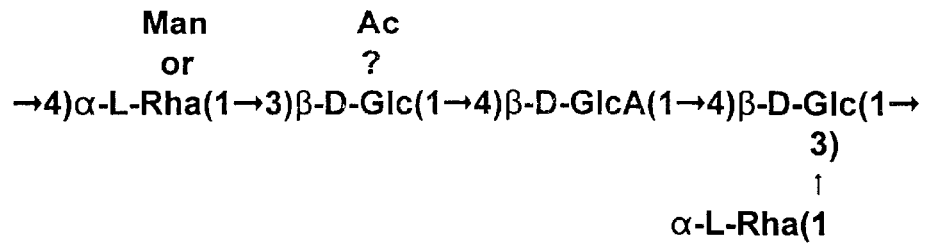

We have discovered new recombinant bacteria for the production of exopolysaccharides. In addition, we have discovered a method for making the recombinant bacteria and making an exopolysaccharide from the bacteria by submerged aerobic fermentation of the bacteria utilizing a sugar substrate. The recombinant bacteria of the present invention are able to produce exopolysaccharides and utilize sugar substrates which are utilizable by the bacteria from which the recombinant bacteria were derived. In addition, the exopolysaccharide obtained from the inventive bacteria exhibit improved, more desirable or different properties from the exopolysaccharide produced by the non-recombinant bacteria from which the recombinant bacteria was derived.

In addition, we have discovered a novel xanthan gum product which as obtained in the broth exhibits reduced cellulase contamination. It is an object of the invention to provide a method of producing bacterial exopolysaccharides by fermentation from sugar substrates that the bacteria which the exopolysaccharides are native to cannot utilize.

It is a further object of the invention to provide a method of increasing the yield of a non-native bacterial exopolysaccharide produced in a recombinant bacterial host.

It is another object of the invention to produce xanthan gum by fermentation from whey waste, a byproduct of cheese production.

Additional objects and advantages of the invention will be set forth in part in the description which follows, and in part will be obvious from the description or may be learned from practice of the invention. The objects and advantages may be realized and attained by means of the methods particularly pointed out in the appended claims.

To achieve the objects and in accordance with the purposes of the present invention, methods for the production of non-native bacterial exopolysaccharides in recombinant bacterial hosts are set forth.

Specifically, we have discovered that the yield of a non-native bacterial exopolysaccharide produced in a recombinant bacterial host can be increased by inactivating the native polysaccharide production in the bacterial host.

DEFINITIONS

As used herein:

"Non-recombinant bacterial host strain" means a bacterial strain which does not contain foreign genetic material.

"Recombinant bacterial host strain" means the non-recombinant bacterial host strain into which foreign genetic material has been introduced and retained. This strain is sometimes referred to herein as the "recipient" or "recipient strain."

"Foreign genetic material" means segments of the genome of a strain of bacteria which are different from those in the recombinant bacterial host strain into which the segment (s) is or is to be introduced.

"Glycosyl transferase" means any one of a group of related enzymes which either catalyze the attachment of a sugar-phosphate molecule to the isoprenyl phosphate carrier involved in exopolysaccharide biosynthesis or the attachment of a sugar to sugars previously attached to the isoprenyl phosphate carrier.

An "sps gene" means one of several genes which are present in the genomes of species of Sphingomonas bacteria or can be isolated from the Sphingomonas bacteria and which are involved in the biosynthesis of a sphingan exopolysaccharide because they code for enzymes that catalyze chemical reactions in the biosynthetic pathway or because they code for proteins or DNA control sites that modulate the amount of sphingan exopolysaccharide present in the bacterial growth medium.

"Non-native exopolysaccharide" means a bacterial exopolysaccharide which is not produced and excreted by a non-recombinant bacterial host strain, but is produced and excreted by a recombinant bacterial host strain obtained from the non-recombinant bacterial host strain.;

"Native bacterial producer" means a non-recombinant bacterial strain which produces the desired bacterial exopolysaccharide.

A "gum gene" means one of several genes which are present in the genomes of species of Xanthomonas bacteria or can be isolated from the Xanthomonas bacterial and which are involved in the biosynthesis of a xanthan exopolysaccharide because they code for enzymes that catalyze chemical reactions in the biosynthetic pathway or because they code for proteins or DNA control sites that modulate the amount of xanthan exopolysaccharide present in the bacterial growth medium.

Examples of two exopolysaccharides, xanthan gum and sphingan S-88 (Jansson, P-E, et al., 1975, Carbohydr Res 45: 275–282, Jansson, P-E, et al., 1986, Carbohydr Res 156: 165–172), are shown by their repeating sugar subunit structures in FIG. 1. The arrows point toward the reducing end of each repeat. For xanthan gum the IP carrier is attached at the reducing end through a phosphodiester linkage to the glucose residue which is lacking the side chain (Ielpi, L, et al., 1993, J Bacteriol 175: 2490–2500). Abbreviations: Glc, glucose; Man, mannose; GlcA, glucuronic acid; Rha, rhamnose; Ac, acetyl ester; and Pyr, acetal-linked pyruvic acid. The position and linkage of the Ac in S-88 is unknown.

DESCRIPTION OF THE PREFERRED EMBODIMENTS

The present invention provides a method of producing a bacterial exopolysaccharide from a sugar source which the native bacterial producer of that exopolysaccharide cannot utilize by transforming a bacterial host strain which can utilize the sugar source but does not produce the exopolysaccharide with genes from the native bacterial producer which are necessary for establishing the production of the exopolysaccharide in the bacterial host strain. The bacterial exopolysaccharide can then be produced by fermenting the recombinant bacterial host with the sugar source. For example, the genes gumBCDEFGHIJKL and M from *X. campestris* strain B1459 were transformed into a specifically mutated Sphingomonas recipient, fermentation of which in the presence of inexpensive waste whey lactose obtained large amounts of secreted xanthan gum which was comparable to that produced by *X. campestris* strain B1459. For production of xanthan gum lacking acetyl side groups, the gumF and gumG genes of Xanthomonas can be omitted from the foreign genetic material obtained from Xanthomonas. Similarly, for production of xanthan gum lacking pyruvyl side groups, the gumL gene can be omitted.

In the case where the "recombinant bacterial host strain" already expresses a gene function that is necessary for production of the "non-native exopolysaccharide", then that function need not be included in the "foreign genetic material". For example, when foreign genetic material is introduced into Sphingomonas bacteria and the initial step in assembly of the repeat subunit structure of the non-native polysaccharide on the isoprenoid lipid carrier is the transfer of glucose-P to the carrier, then any of several gene functions that carry out the same specific enzymatic reaction can be substituted. For example, in place of the gumD gene of Xanthomonas species on could substitute the spsB gene from Sphingomonas species or the pssA gene from Rhizobium species, or analogous genes from other bacteria.

The present invention further provides a method for increasing the yield of a non-native exopolysaccharide produced in a recombinant bacterial host strain by inactivating the exopolysaccharide production native to the bacterial host strain. Preferably, the inactivation is achieved by deletions or mutations in the genome of the bacterial host strain. Most preferably, the deletion or mutation inactivates the activity of a glycosyl transferase.

Most preferably, the deletion or mutation inactivates the activity of a glycosyl transferase, a polysaccharide polymerase, a secretory apparatus, or enzymes required for the synthesis of essential nucleotide-sugar precursors. For example, in Sphingomonas, inactivation of one or more of the essential substrate-specific glycosyl transferase enzymes, such as, spsB, Q, K or L, which are required for synthesis of the subunit sugar repeat structure which is attached to the carrier C55-isoprenyl phosphate eliminates synthesis of the polysaccharide produced by Sphingomonas. Likewise, mutations in a polysaccharide polymerase or in a secretion apparatus also eliminate exopolysaccharide production by a native polysaccharide producer. Production of the native polysaccharide can also be eliminated by mutations which inactivate enzymes that are essential for the synthesis of precursor nucleotide-sugars, such as the four enzymes required to synthesize the precursor dTDT-L-rhamnose:RhsA, RhsB, RhsC, or RhsD. The mutations or deletions which eliminate these enzyme or protein activities can either directly inactivate these enzymes by altering the structures and activities of the enzymes or indirectly inactivate the enzymes by blocking or modulating the expression of the genes that code for these enzymes or proteins.

The present invention also provides a method for minimizing contaminating cellulase activity in xanthan gum produced by fermentation by fermenting a recombinant Sphingomonas species strain transformed with genes from the genome of *X. campestris*, which are necessary for establishing the production of xanthan gum in the Sphingomonas species.

All of the embodiments use the following bacterial strains, recombinant DNA procedures, and growth media:

Strain X59 (ATCC 55298—see U.S. Pat. No. 5,194,386, col. 8–9) is a spontaneous rifampicin-resistant mutant derived from wild type *X. campestris* B 1459 (Thorne, L, et al., 1987, J Bacteriol 169: 3593–3600). Cloned DNA segments and site-specific chromosomal deletions are diagramed in FIG. 2. Plasmid XCc8 is a member of a cosmid library (Thorne, L, et al., 1987, J Bacteriol 169: 3593–3600) and was obtained by inserting a segment of about 24 kilobase pairs (kbp) of chromosomal DNA from strain X59 into the mobilizable broad-host-range plasmid vector pRK311 (Ditta, G, et al., 1985, Plasmid 13: 149–153). The DNA segment carried by plasmid XC600(gumB-M) was derived from plasmid XCc8 by standard methods of DNA isolation, digestion with restriction endonucleases, and ligation (Maniatis, T, et al., 1982, Molecular cloning: a laboratory manual. Cold Spring Harbor Laboratory, Cold Spring Harbor). The insert in plasmid XC600 spans the NdeI-SalI segment of XCc8 corresponds to nucleotide 919–15400 of the gum sequence in GenBank accession number U22511, shown in Seq. ID No.1 hereof. (GenBank, National Center for Biotechnology Information, National Library of Medicine, Bethesda, Md. 20894, www.ncbi.nlm.gov/web/genbank). Plasmid XC1483 includes nucleotide 3460 (BamHI) through 7959 (BamHI) (Pollock, T J, et al., 1994, J Bacteriol 176: 6229–6237). Plasmids S88cl, and S88c3 are members of a cosmid library (Yamazaki, M, et al., 1996, J Bacteriol 178: 2676–2687) that were derived from a partial digestion with SalI enzyme of S88 chromosomal DNA, followed by ligation to the vector pRK311. The nucleotides deleted in strain S88ΔTn358 include 4485 (BamHI) through 24646 (EcoRI) in the S88 sequence (GenBank accession U51197 Seq. ID No. 2 hereof). Strain S88m265 is defective in spsB (Yamazaki, M, et al., 1996, J Bacteriol 178: 2676–2687).

DNA transformation into *E. coli*, tri-parental conjugal mating of broad-host-range plasmids into Sphingomonas or *X. campestris*, and selection methods were described (Yamazaki, M, et al., 1996, J Bacteriol 178: 2676–2687).

Luria-Bertani and M9 salts are standard media (Pollock, T J, et al., 1994, J Bacteriol 176: 6229–6237). M9+YE is M9 salts supplemented with 0.05 % w/v yeast extract. YM medium contains 3 g Bacto yeast extract, 3 g malt extract, 5 g Bacto peptone, and 10 g D-glucose per liter of deionized water. ¼ YM-G medium is YM diluted with 3 volumes of water and with no added glucose. The amounts of antibiotics used were as follows: rifampicin, 50 mg L$^{-1}$; streptomycin, 50 mg L$^{-1}$; kanamycin, 50 mg L$^{-1}$; and tetracycline, 6–15 mg L$^{-1}$ (Sigma Chemical Co.). Low viscosity carboxymethylcellulose (1% w/v final, Sigma Chemical Co.) was mixed with TSA blood agar base (Difco), and then cultures were spotted onto the surface of the medium and grown for 4–7 days at 30° C. Zones of hydrolysis of carboxymethylcellulose were observed by gently flooding the plate with 0.1% (w/v) Congo red dye for 30 min followed by destaining with 1M NaCl for 30 min. The diameters of the zones were then measured to compare the relative cellulase activity of the various cultures.

The following chemical and physical analyses of exopolysaccharides were used in the examples:

Extracellular xanthan gum or sphingan S-88 was precipitated from liquid culture medium with 2–3 volumes of isopropyl alcohol, and then dried at 80° C. before weighing. Hydrolysis mixtures contained 0.5–5 mg of polysaccharide and 130–260 μl 2M (v/v) trifluoroacetic acid in high performance liquid chromatography (HPLC) water, and were incubated for 16 h at 95° C. The samples were dried under vacuum, resuspended in 100 μl HPLC water, dried again, and finally resuspended in 100 μl of HPLC water. Samples and sugar standards were separated on a CarboPac PA-1 anion-exchange column and the sugar compositions were quantitated with a Dionex DX500 HPLC system as described previously (Clarke, A J, et al., 1991, Anal Biochem 199: 68–74). Assays for acetyl (Hestrin, S, 1949, J Biol Chem 180: 249–261) and pyruvyl (Duckworth, M, et al., 1970, Chem Ind 23: 747–748) groups have been described.

Samples of polysaccharides (10 mg, powdered) were dissolved in 2 ml deionized water at 80° C. for 60 min in glass test tubes with an equal weight of locust bean gum and bromphenol blue dye (100 μg ml$^{-1}$). After cooling for 2 h the tubes were rotated to horizontal for photography. Failure to gel resulted in horizontal movement of the mixed slurry.

A sample of commercial xanthan gum (Keltrol, Kelco Company) was used for physical and chemical comparisons.

For xanthan-guar mixtures each polysaccharide was dissolved in 100 mM KCl at 0.1% w/v, and solution viscosities were measured at 20–25° C. at several rpm with a Brookfield LVTDV-II viscometer and spindle 18.

Deposits

The following deposits have been made in connection with the present invention:

1. Sphingomonas paucimobilis (ATCC 29837) containing plasmid XCc8 ATCC Designation No. 98479;
2. Sphingomonas strain S88ΔTn358 containing plasmid XCc8 ATCC Designation 98480.

The above deposits were made with the American Type Culture Collection located at 10801 University Blvd., Manassas, Va. 20110–2209m pursuant to the Budapest Treaty for the International Recognition of the Deposit of Microorganisms for the Purposed of Patent Procedure. All restrictions on the availability of the materials deposited will be irrevocably removed upon the issuance of a patent thereon.

All other microorganisms and/or DNA segments, plasmids, and the like referred to herein are publicly available from the American Type culture collection in Manassas, Va.

EXAMPLE 1

Inter-Generic Expression of Genes Coding for Polysaccharide Biosynthesis

Figure 2:
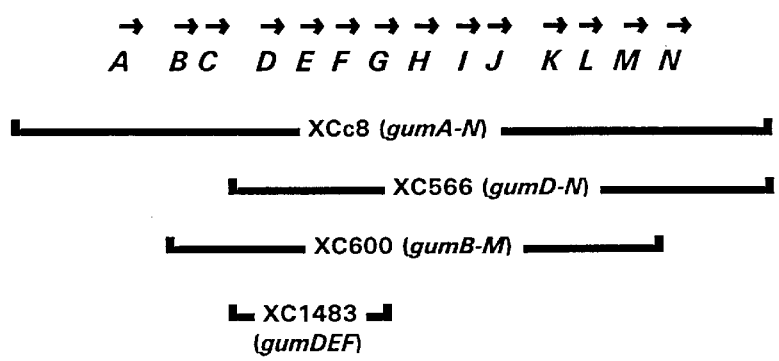
FIG. 2 is a schematic map of the *X. campestris* gum and Sphingomonas S88 sps genes.
Figure 2:
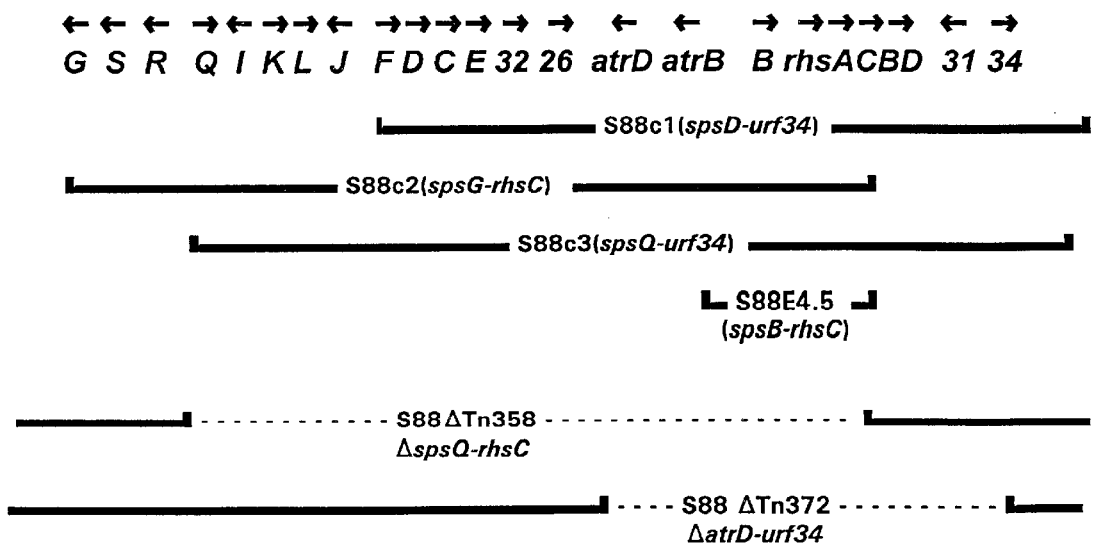

Referring to FIG. 2, maps of *X. campestris* gum and Sphingomonas S88 sps genes, boundaries of specific segments cloned in plasmids, and deletions in bacterial chromosomes are shown. The arrows above the genes indicate the direction of transcription. The horizontal lines indicate the extent of the cloned DNA included in each plasmid with the included genes within parentheses. The dashed lines indicate the regions deleted from mutant chromosomes. The gumB through M genes (GenBank accession U22511) span about 14 kbp and the spsG through urf34 genes (GenBank accession U51197)include about 29 kbp.

The original cosmid clones and specific subcloned segments (diagramed in FIG. 2) were transferred by conjugal mating into *X. campestris* and Sphingomonas recipients. The type of EPS secreted into the medium was determined from the appearance of colonies and liquid cultures, and from the physical properties and carbohydrate compositions of the recovered polysaccharides.

As described in Table 1 and the legend, *X. campestris* X59 (Gum$^+$), Sphingomonas S88 (Sps$^+$) and the polysaccharide-negative mutant S88m265 (Sps$^-$), have readily distinguished colony morphologies and characteristics in liquid culture. From a visual inspection, one can not only determine if any EPS is being secreted, but also whether the EPS is sphingan S-88 or xanthan gum. EPS samples were acid hydrolyzed, and the identity and amounts of monosaccharide(s) were determined. The xanthan gum secreted from *X. campestris* contained two neutral sugars, with glucose representing about 67% and mannose about 33% of the sum of the peak areas for the neutral sugars on the HPLC chromatograms. By contrast, sphingan S-88 contained about 18% rhamnose, 59% glucose, and 23% mannose. The sugar components distinguished xanthan gum from sphingan S-88.

The colonial appearance (Sps$^+$) and composition of neutral sugars from the polysaccharides secreted by the recipient S88m265 carrying plasmid S88c1 indicated that the plasmid, which carries a normal spsB gene, restored sphingan S-88 synthesis to the mutant. Plasmid XC 1483 with the *X. campestris* gumD gene also restored sphingan S-88 synthesis to S88m265.

Of particular interest is that a mixture of neutral sugars composed of about one-fourth sphingan S-88 and three-fourths xanthan gum was obtained when plasmid XCc8, which carries gum genes, was introduced into S88m265. This recombinant strain has all of the genes needed to make both exopolysaccharides in strain S-88. Thus, with the present invention, it is possible to obtain two different exopolysaccharides from the same organism at the same time.

TABLE 1

Sugar compositions of bacterial exopolysaccharides

| Donor plasmids | Bacterial recipient and phenotype | Recombinant phenotype$^a$ | Rha | Glc | Man |
|---|---|---|---|---|---|
| — | *X. campestries* X59 Gum$^+$ | | 0 | 67 | 33 |
| — | Sphingomonas S88 Sps$^+$ | | 18 | 59 | 23 |
| S88c1 | S88m265 (SpsB$^-$) | Sps$^+$ | 19 | 62 | 19 |
| XC1483 | " | Sps$^+$ | 22 | 61 | 17 |
| XCc8 | " | Sps/Gum$^+$ | 7 | 64 | 29 |
| S88c3 | S88ΔTn358(Sps$^-$) | Sps$^+$ | 19 | 63 | 19 |
| XCc8 | " | Gum$^+$ | 0 | 64 | 36 |
| XC600 | " | Gum$^+$ | 0 | 62 | 37 |
| XC566 | S88ΔTm372(Sps$^-$) | Gum$^-$ | | | |
| XCc8 | S88m134(SpsB$^-$ RhsD$^-$) | Gum$^+$ | | | |
| XCc8 | *S. paucimobilis* ATCC 29837 | Gum$^+$ | | | |

$^a$Gum$^+$ indicates a wild-type *X. campestris*-like appearance caused by the secretion of viscous xanthan gum, with large (3–5 mm in four days at 30° C.), shiny, mucoid, light-yellow-colored colonies on solid YM medium and a viscous culture broth in liquid YM medium with non-aggregated cells.
Sps$^+$ indicates a wild-type appearance typical of Sphingomonas strains secreting a capsular sphingan polymer: colonies are opaque to transmitted light, shiny but not viscous, and produce viscous liquid culture broths containing aggregates of cells.

By deleting certain sps genes from the S88 chromosome we obtained synthesis in Sphingomonas of xanthan gum alone. Although plasmid S88c3 (sps genes) restored synthesis of sphingan S-88 to the deletion mutant S88ΔTn358, plasmids XCc8 and XC600 (gum genes) caused the synthesis of a polysaccharide that matched the neutral sugar percentages of xanthan, and lacked rhamnose.

Plasmid XCc8 caused the synthesis of only xanthan gum in a double mutant of Sphingomonas (S88m134) which has defects in glucosyl-IP transferase (SpsB$^-$) and in synthesis of the essential dTDP-rhamnose substrate (RfbD$^-$). We also observed xanthan gum synthesis in the type strain for the *S. paucimobilis* genus, ATCC 29837, which otherwise does not secrete any polysaccharide. Physical studies on this polysaccharide detailed in Example 3 confirmed that it was xanthan gum.

EXAMPLE 2

Detection of Gene Function in Recombinants

In order to determine if the acetylase (gumF and G) and pyruvylase (gumL) genes of *X. campestris* were functioning in Sphingomonas we measured the amounts of each component for samples of the recombinant and commercial xanthan gums. The degree of acetylation for the recombinant sample (S88ΔTn358 with plasmid XCc8) exceeded that for the commercial xanthan gum by a few percent and was similar to the degree of acetylation for xanthan gum made by *X. campestris* X59 while growing under the same conditions as the recombinant Sphingomonas. The recombinant samples were 4–6% by weight as pyruvate compared to 5–6% for commercial xanthan (Keltrol) and xanthan made by *X. campestris* X59.

EXAMPLE 3

Physical Analyses of Recombinant Xanthan Gum

Three physical properties of recombinant and commercial xanthan gum were compared. First, the viscosity synergism expected for mixtures of xanthan and guar gums was observed for the recombinant samples (Table 2). Solution viscosities were measured for samples with and without added guar gum. The viscosities of the mixtures of guar gum with either commercial xanthan gum or the recombinant samples were higher than the sum of the viscosities of the unmixed polysaccharides. Second, xanthan gum is unique in forming a rigid gel in the presence of locust bean gum. Rigid gels were formed by mixing locust bean gum with commercial xanthan gum or with any one of three recombinant samples: plasmid XCc8 in either S88m265, S88ΔTn358, or *S. paucimobilis* ATCC 29837. Third, the viscosity of each recombinant xanthan sample was shear thinning like commercial xanthan gum. These three physical tests confirmed that the EPS secreted by the recombinant Sphingomonas strains was comparable to xanthan gum.

TABLE 2

Viscosity synergism for mixtures of exopolysaccharides and guar gum

| | Viscosity (cp)$^a$ | |
|---|---|---|
| EPS | EPS alone | EPS with guar |
| None | — | 4 |
| xanthan gum | 22 | 49 |
| X59 | 27 | 63 |
| S88m265/XCc8 | 7 | 18 |
| S88ΔTn358/XCc8 | 9 | 27 |
| ATCC29837/XCc8 | 7 | 29 |

$^a$Centipoise (cp) for spindle 18 at 12 rpm for final concentrations of each polymer at 0.1% in 100 mM KCl at room temperature

EXAMPLE 4

Alternative Culture Conditions

The results in Table 3 indicate that the recombinant Sphingomonas strains, in contrast to *X. campestris*, converted either lactose or glucose to xanthan gum to a similar extent.

TABLE 3

Cell densities and xanthan gum yields for shake flask cultures.

| Growth medium, temperature, and sugar substrate | X59 | | S88ΔTn358 with XCc8 | | ATCC 29837 with XCc8 | |
|---|---|---|---|---|---|---|
| | A600 | mg | A600 | mg | A600 | mg |
| 1/4 YM – G | | | | | | |
| 30° C. glucose | 1.1 | 43 | 6.0 | 62 | 2.9 | 37 |
| 33° C. glucose | 0.8 | 34 | 4.8 | 49 | 2.6 | 33 |
| 30° C. lactose | 0.4 | 16 | 5.4 | 67 | 3.4 | 39 |
| M9 + YE | | | | | | |
| 30° C. glucose | 2.4 | 84 | 2.1 | 30 | 4.9 | 55 |
| 30° C. lactose | 0.2 | 9 | 2.3 | 30 | 6.3 | 53 |

1/4 YM-G and M9 + YE were supplemented with either glucose or lactose to 2% w/v. Culture density was measured as the absorbance at 600 nm. The yield of xanthan gum (mg) is the average for samples of 10 ml taken from two separately inoculated flasks after 48 h (1/4YM-G) or 42 h (M9 + YE). The cultures were centrifuged to remove cells before precipitation of the polysaccharides with alcohol.

Production rates and yields for large scale xanthan gum fermentations are sensitive to temperature and aeration. The highly viscous broth requires considerable stirring and cooling to achieve maximum productivity. Although *X. campestris* produces xanthan gum optimally at about 28° C., Sphingomonas strains are known to grow at temperatures up to about 37° C.

As shown in Table 3, the recombinant Sphingomonas strains grew at 30° C. and 33° C. In the case of recombinant ATCC 29833 with XcC8, the yields of gum were about equivalent to the native gum producer X-59 at both 30° C. and 33° C. in ¼YM-G media. However, the case of the recombinant S88ΔTn358 with XCc8 in ¼YM-G media, the yields of gum were significantly above those of the native gum producer X59 at both temperatures.

This is an important aspect of the present invention since, as the fermentation is exothermic, a major energy requirement is cooling of the fermentation broth. With the present invention, the fermentation can be carried out at a higher temperature, in the range from about 30 to 33° C. This means that less cooling is required and a substantial energy cost savings can be realized with the present invention as compared with the conventional fermentation conditions used for xanthan gum production.

EXAMPLE 5

Reduction of Cellulase Contamination in Xanthan Gum

The presence of contaminating cellulase in xanthan gum is disadvantageous in commercial applications where xanthan is mixed with or contacts cellulosic polymers. As judged by measuring the zones of hydrolysis surrounding cultures spotted onto agar plates containing carboxymethylcellulose, we found that the inventive Sphingomonas recombinants showed less than one-eighth of the cellulase activity observed for *X campestris* strain X59. This means that xanthan gum as produced from the inventive strains contains significantly decreased amounts of contaminating cellulase as compared with xanthan gum obtained from X59. As used herein, "as produced" means the xanthan product as obtained directly from the broth without any steps, after-treatments or procedures taken to remove cellulase therefrom. Accordingly, the as produced xanthan gum obtained with the present invention is advantageous since it avoids the increased costs and steps normally required with conventional xanthan product to remove or decrease the cellulase content.

It is to be understood that the foregoing examples are exemplary and explanatory only and are not restrictive of the invention. Various changes may be made to the embodiments described above by one of skill in the art without departing from the scope of the invention, as defined by the following claims.

We claim:

1. A method for making a recombinant xanthan producing Sphingomonas species strain, comprising transferring a portion of the genome of *Xanthomonas campestris* into a Sphingomonas species, the genome portion comprising a set of genes selected from the group consisting of the gumB, gumC, gumD, gumE, gumF, gumG, gumH, gumI, gumJ, gumK, gumL and gumM genes of the *X. campestris* genome, wherein the transfer of the set of genes enables recombinant xanthan production in the Sphingomonas species.

2. The method of claim 1, wherein the genome portion comprises the gumB, gumC, gumD, gumE, gumF, gumG, gumH, gumI, gumJ, gumK, gumL and gumM genes.

3. The method of claim 1, wherein the genome portion is on a plasmid.

4. The method of claim 1, wherein the genome portion is integrated into the Sphingomonas species' genome.

5. The method of claim 1, further comprising inactivation of native sphingan production in the Sphingomonas strain by deletion or mutation of one or more of the Sphingomonas strain's sps genes.

6. A recombinant Sphingomonas species strain made by the method of claim 1, which produces and secretes xanthan gum into media in which the recombinant Sphingomonas species is grown.

7. A method of producing xanthan gum from lactose, comprising incubating a recombinant Sphingomonas species strain in a media containing lactose and harvesting the xanthan gum from the media, wherein the recombinant Sphingomonas species strain is made by the method of claim 1.

8. The method of claim 7, wherein the lactose of the media is provided as a whey waste byproduct of cheese production.

9. A method for making xanthan gum comprising subjecting a recombinant Sphingomonas species strain to submerged aerobic fermentation conditions and harvesting the xanthan gum from the fermentation, wherein the recombinant Sphingomonas species strain is made by the method of claim 1.

10. The method of claim 9 wherein the fermentation is carried out at a temperature in the range from about 30 to 33° C.

11. Strain ATCC 98479.

12. Strain ATCC 98480.

13. A recombinant Sphingomonas species strain made by the method of claim 2, which produces and secretes xanthan gum into media in which the recombinant Sphingomonas species is grown.

14. A recombinant Sphingomonas species strain made by the method of claim 3, which produces and secretes xanthan gum into media in which the recombinant Sphingomonas species is grown.

15. A recombinant Sphingomonas species strain made by the method of claim 4, which produces and secretes xanthan gum into media in which the recombinant Sphingomonas species is grown.

16. A recombinant Sphingomonas species strain made by the method of claim 5, which produces and secretes xanthan gum into media in which the recombinant Sphingomonas species is grown.

17. A method of producing xanthan gum from lactose, comprising incubating a recombinant Sphingomonas species strain in a media containing lactose and harvesting the xanthan gum from the media, wherein the recombinant Sphingomonas species strain is made by the method of claim 2.

18. The method of claim 17, wherein the lactose of the media is provided as a whey waste byproduct of cheese production.

19. A method of producing xanthan gum from lactose, comprising incubating a recombinant Sphingomonas species strain in a media containing lactose and harvesting the xanthan gum from the media, wherein the recombinant Sphingomonas species strain is made by the method of claim 5.

20. The method of claim 19, wherein the lactose of the media is provided as a whey waste byproduct of cheese production.

21. A method for making xanthan gum comprising subjecting a recombinant Sphingomonas species strain to submerged aerobic fermentation conditions and harvesting the xanthan gum from the fermentation, wherein the recombinant Sphingomonas species strain is made by the method of claim 2.

22. A method for making xanthan gum comprising subjecting a recombinant Sphingomonas species strain to submerged aerobic fermentation conditions and harvesting the xanthan gum from the fermentation, wherein the recombinant Sphingomonas species strain is made by the method of claim 5.

23. Xanthan gum as produced by the method of claim 9 and having substantially reduced cellulase activity relative to xanthan gum produced from strain X59 by submerged aerobic fermentation and harvesting from the fermentation.

24. The xanthan gum of claim 23 which has at least 50 percent less cellulase activity relative to xanthan gum produced from strain X59.

* * * * *